US009389064B2

(12) United States Patent  (10) Patent No.: US 9,389,064 B2
Liu et al.  (45) Date of Patent: Jul. 12, 2016

(54) INLINE INSPECTION OF THE CONTACT BETWEEN CONDUCTIVE TRACES AND SUBSTRATE FOR HIDDEN DEFECTS USING WHITE LIGHT INTERFEROMETER WITH TILTED OBJECTIVE LENS

(71) Applicant: Intel Corporation, Santa Clara, CA (US)

(72) Inventors: Shuhong Liu, Chandler, AZ (US); Zhiyong Wang, Chandler, AZ (US); Nilanjan Ghosh, Chandler, AZ (US); Deepak Goyal, Phoenix, AZ (US)

(73) Assignee: Intel Corporation, Santa Clara, CA (US)

( * ) Notice: Subject to any disclaimer, the term of this patent is extended or adjusted under 35 U.S.C. 154(b) by 81 days.

(21) Appl. No.: 14/229,446

(22) Filed: Mar. 28, 2014

(65) Prior Publication Data

US 2015/0276375 A1 Oct. 1, 2015

(51) Int. Cl.
*G01B 11/02* (2006.01)
*G01B 9/02* (2006.01)
*G01B 11/06* (2006.01)
*G01N 21/956* (2006.01)
*G02B 21/00* (2006.01)

(52) U.S. Cl.
CPC ............ *G01B 9/0203* (2013.01); *G01B 9/0209* (2013.01); *G01B 11/0675* (2013.01); *G01N 21/956* (2013.01); *G02B 21/0016* (2013.01); *G01B 2210/56* (2013.01)

(58) Field of Classification Search
CPC ........ G01B 11/30; G01F 7/0591; G01F 7/706
USPC .................................... 356/497, 237.1–237.5
See application file for complete search history.

(56) References Cited

U.S. PATENT DOCUMENTS

| 6,449,048 B1 * | 9/2002 | Olszak | G01B 11/2441 356/497 |
| 2011/0113619 A1 * | 5/2011 | Viscarra | H01Q 21/0087 29/600 |

OTHER PUBLICATIONS

"White Light Inferometry"—Wikipedia®, http://en.wikipedia.org/wiki/White_light_interferometry, Feb. 17, 2014. (4 pages).

* cited by examiner

*Primary Examiner* — Jonathan Hansen
(74) *Attorney, Agent, or Firm* — Blakely, Sokoloff, Taylor & Zafman LLP

(57) ABSTRACT

Embodiments include devices, systems and processes for using a white light interferometer (WLI) microscope with a tilted objective lens to perform in-line monitoring of both resist footing defects and conductive trace undercut defects. The defects may be detected at the interface between dry film resist (DFR) footings and conductive trace footing formed on insulating layer top surfaces of a packaging substrate. Such footing and undercut defects may other wise be considered "hidden defects". Using the WLI microscope with a tilted objective lens provides a high-throughput and low cost metrology and tool for non-destructive, non-contact, in-line monitoring.

12 Claims, 12 Drawing Sheets

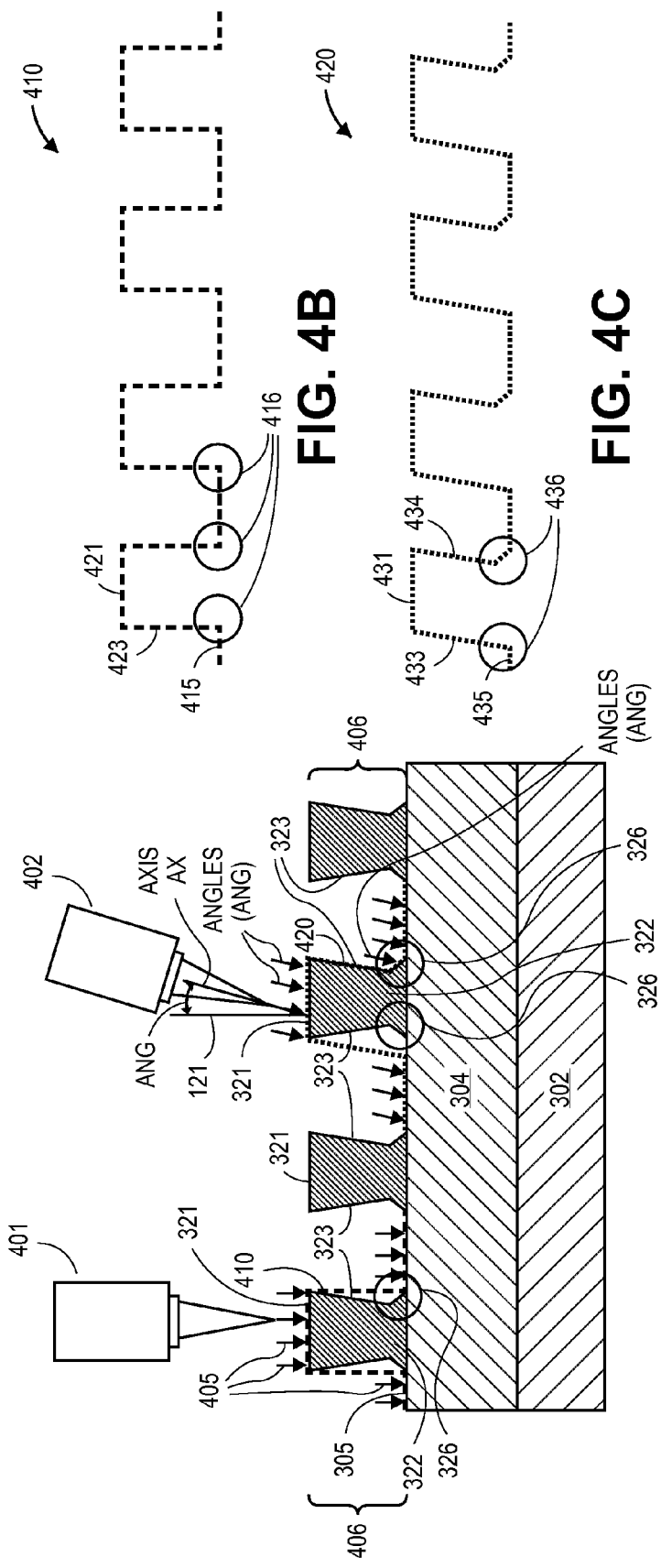

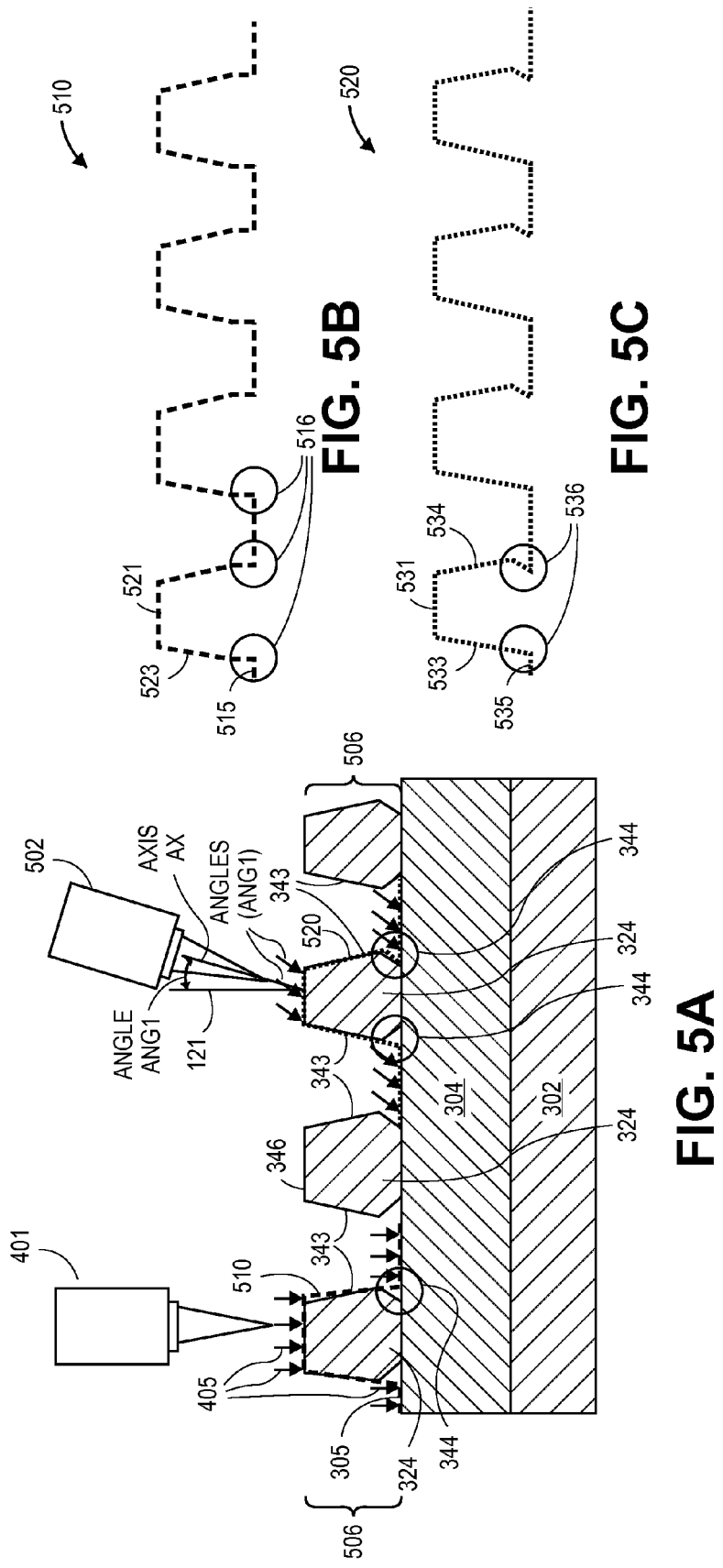

INLINE INSPECTION OF THE CONTACT BETWEEN CONDUCTIVE TRACES AND SUBSTRATE FOR HIDDEN DEFECTS USING WHITE LIGHT INTERFEROMETER WITH TILTED OBJECTIVE LENS

BACKGROUND

1. Field

Embodiments of the invention are related to inspecting the interface or contact between lithographic resist film (e.g., dry film resist (DFR)) and conductive traces formed on the top surface of an insulating substrate such as for a chip package, for film footing defects and conductive trace undercut (CUT) defects.

2. Description of Related Art

One of the key issues resulting in high yield loss in substrate package technology development (SPTD) or bump-less build-up layer (BBUL) packaging is missing or lifted conductor (e.g., Copper—Cu) traces formed on the top surface of an insulating substrate (e.g., microprocessor packaging substrate, or a substrate having a surface of dielectric, insulator, or ajinomoto build-up film (ABF)). Yield loss as high as 70% due to this issue has been observed. Key contributors for missing or lifted conductive traces include "hidden defects" such as dry film resist (DFR) footing defects of film patterned to form the traces; and conductive trace undercut (CTU) defects of traces formed on the substrate. Large DFR and CTU defects can result in smaller contact area between conductive traces and insulating substrate, and thus cause conductive trace to lift off in downstream process. Such liftoff can result in damaged, destroyed or missing lengths of the conductive traces, often causing undesired open circuits in the trace circuitry.

Therefore, inspecting DFR footing and CTU can be a key step for process control and prevention of yield loss and reliability issues during SPTD process development. Developing non-destructive non-contact measurement solution for such defects is inherently challenging due to the hidden nature and small dimension of the defects. Current inline monitoring tools (e.g., tools that can be used while or after the traces are formed and prior to subsequent processing of the package) such as X-ray and acoustic microscopy do not have the capability to image and screen such defects due to low contrast or resolution of the interface or contact between conductive traces and substrate. So far the only method available to assess DFR and CTU defects is non in-line, physical failure analysis (FA), cross-section which is destructive to the substrate and has low-throughput due to the time required to cut the substrate. Thus, this method is not amenable to inline process monitoring or inspection of the interface, such as inspection during manufacture or processing to create packages during SPTD or BBUL. What is needed is a high-throughput and low cost metrology tool for non-destructive, non-contact in-line monitoring of both DFR and CTU defects.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one.

FIG. 4A shows an inspection setup for inspecting the top surface of the insulating substrate, the side surface of the resist islands, and the top surface of the resist islands of FIG. 3C to detect resist islands footing defects using a WLI microscope.

FIG. 4B shows a surface profile using a WLI microscope at a vertical or 90 degree angle, with respect to a top surface of the FIG. 4A surface.

FIG. 4C shows a surface profile using a tilted WLI microscope at a non-vertical or angle of between 70 and 88 degree with respect to a top surface of the FIG. 4A surface.

FIG. 5A shows an inspection set up for inspecting the top surface of the insulating substrate, the side surface of the conductive trace, and the top surface of the conductive trace of FIG. 3E to detect conductor trace undercut (CUT) defects using a WLI microscope.

FIG. 5B shows a surface profile using a WLI microscope at a vertical or 90 degree angle, with respect to a top surface of the FIG. 5A surface.

FIG. 5C shows a surface profile using a tilted (1) surface and (2) WLI microscope or an "objective" of a WLI microscope at a non-vertical or angle of between 70 and 85 degrees with respect to a top surface of the FIG. 5A surface.

DETAILED DESCRIPTION

Figure 1A:
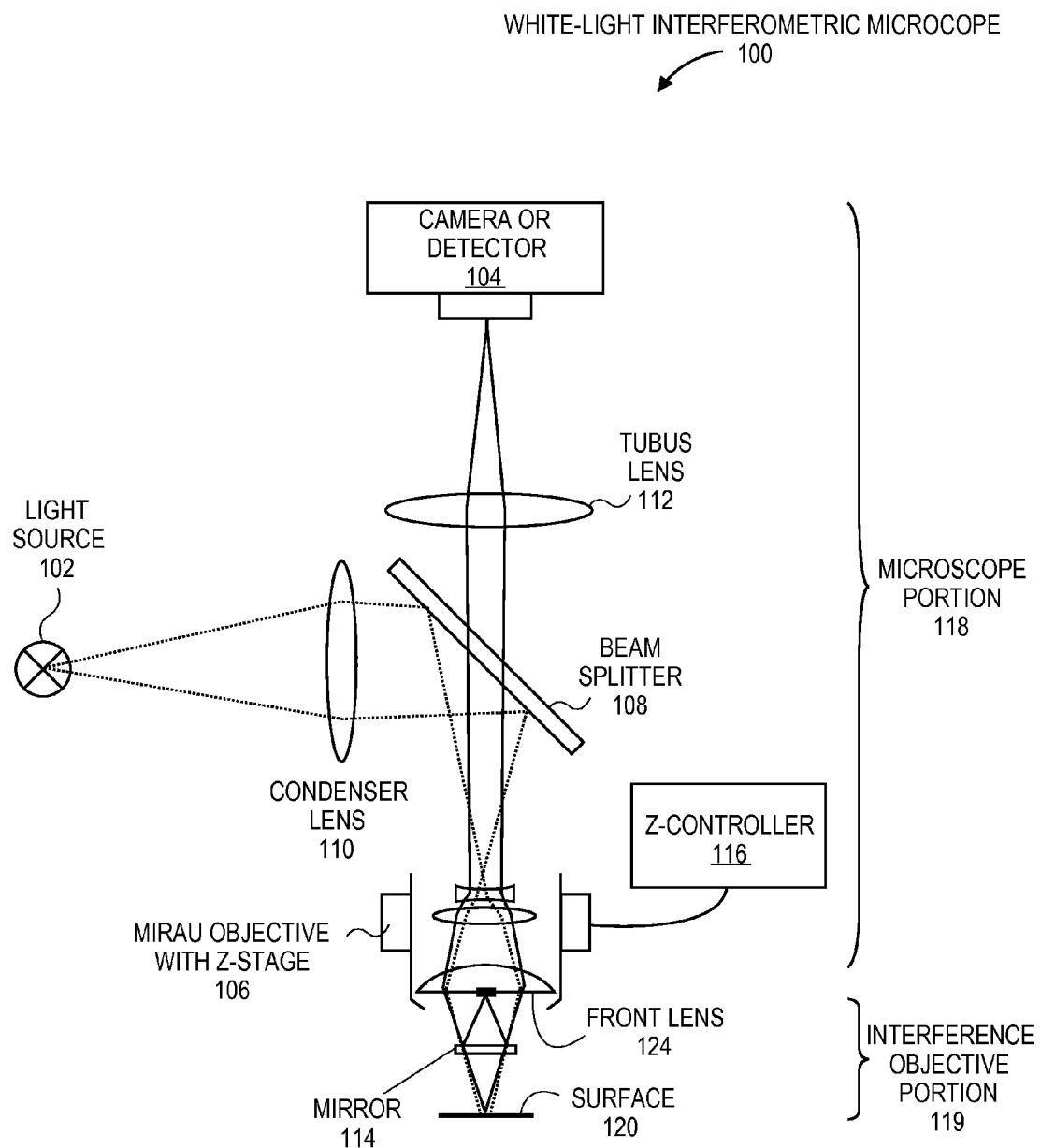
FIG. 1A is a schematic cross-sectional view of a white-light interferometric (WLI) microscope capable of surface profile measurements using the principle of interferometry.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

Currently no inline metrology tool exists in the industry that can be used to measure dry film resist (DFR) footing or conductive trace undercut (CTU) defects in-line during in substrate package technology development (SPTD) or bumpless build-up layer (BBUL) processes. Embodiments of the invention are related to inspecting the interface or contact between dry film resist (DFR) and/or conductive traces formed on the top surface of an insulating substrate (e.g., ABF), for DFR footing defects and/or conductive trace undercut (CUT) defects. Such defects may include missing or lifted conductor (e.g., Copper—Cu) traces formed on the top surface of an insulating substrate (e.g., such as a substrate used in of an electronic device package, a microprocessor package, or a substrate having a surface of dielectric, insulator, or ajinomoto build-up film (ABF).

More specifically, embodiments of the invention provide a solution to image such defects using white light interferometry (WLI) (e.g., a WLI microscope) with tilted objective lens setup. WLI offers the capability of surface profile measurement (e.g., increased X,Y and Z resolution) using the principle of interferometry, while tilted objective lens allows the inspection or detection of features or defects in hidden areas. Such features or defects includes those in hidden areas, such as features or defects in the X,Y or Z direction (1) that extend away or outwards in the X,Y direction from, and are along the X,Y direction base or interface of Z height DFR islands, and/or (2) that extend towards or into the X,Y direction base or interface of Z height conductive traces. In other words, these defects can be 3 dimensional with an X,Y direction component and a Z height direction component that (1) originates at the base or interface of a DFR island (and extend outwards from the side surface of a DFR island, adding or increasing DFR material at the base or interface), or (1) originates at the base or interface of the conductive trace (and extend inwards from the side surface of a conductive trace, removing or reducing conductive trace material at the base or interface).

Embodiments of the invention provide several advantages or benefits as compared to the known solutions, such as by providing inspecting for or detecting such defects while being: 1) Non-contact and non-destructive; 2) High resolution; 3) In-line process monitoring capability; 4) Large area inspection; and/or 5) High throughput and significant cost reduction.

FIG. 1A is a schematic cross-sectional view of a white-light interferometric (WLI) microscope capable of surface profile measurements using the principle of interferometry. The basic principle of a WLI microscope may be shown in FIG. 1A. FIG. 1A shows WLI microscope 100 including light source 102 illuminating beam splitter 108 through condenser lens 110. The light is split by beam splitter to be directed towards camera or detector 104 and Tubus lens 112. In some cases, lens 110 may be used or designed to focus light from the illumination source 102 onto the object lens 124, or onto surface 120 through objective 106 or portion 119. In some cases, lens 112 may be used or designed to converge parallel light to form images, such as by converging or focusing onto detector 104$m$ light received from object lens 124, or from surface 120 through objective 106 or portion 119. The light from source 102 is also split by splitter 108 towards Mirau objective with Z-stage 106, for illuminating surface to be examined 120 through mirror 114. Mirau objective with Z-stage 106 includes Z-controller 116 for controlling Z height of Z-stage 106 (e.g., lens 124). In some cases, surface to be examined 120 is or includes a surface of a substrate (e.g., surface 305 of substrate 304 described below) having DFR (e.g., islands 322 described below) or conductive traces (e.g., traces 324 described below); or a surface of a platform to hold such a substrate (e.g., a platform upon which substrate 300, or a substrate including insulating layer 304, islands 322 or traces 324 is disposed or mounted).

As known a principle of interferometry includes the superposition of waves, the waves being split by a beam splitter. The distance of the lens to the surface (or surface of the platform) may be fixed within a range that is appropriate for the proper superposition of waves to provide images as described herein.

Figure 1B:
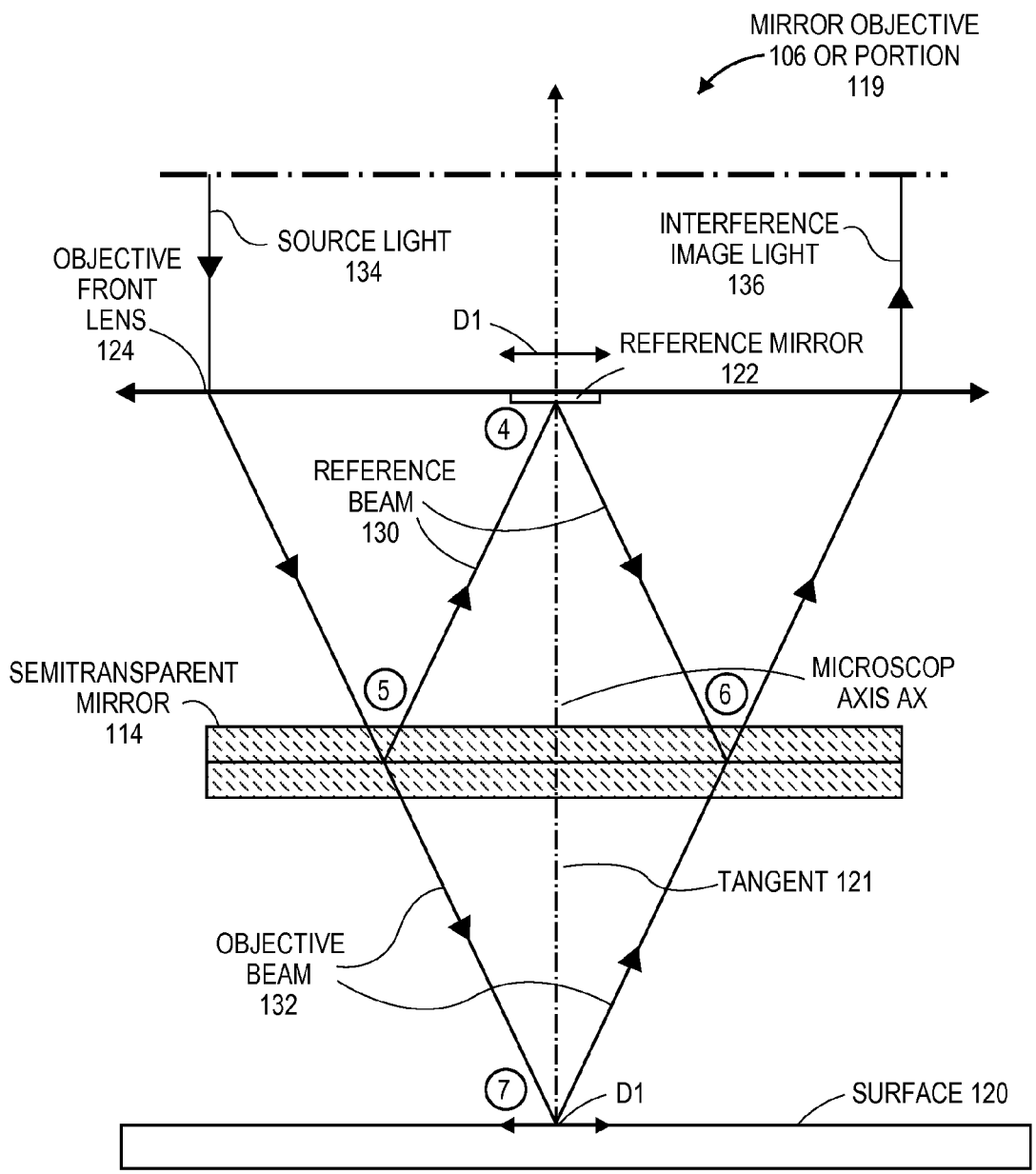
FIG. 1B is a schematic cross-sectional schematic diagram of a Mirau objective portion of a WLI microscope.

FIG. 1B is a schematic cross-sectional schematic diagram of a Mirau objective portion 119 of microscope 100. Mirau objective portion 119 includes objective or front lens 124 of the microscope, semitransparent mirror 114, reference mirror 122 (mounted on bottom surface of lens 124) with reference beam 130, first reflection of reference beam (5), third reflection of reference beam (6), and reflection of object beam (7). It may or may not include surface 120.

FIG. 1B shows portion 119 having reflections or light beams 1, 2, 3, 4, 5, 6 and 7. Source light 134 may be incident light from light source 102 and splitter 108 received from splitter 108 by Z-stage 106 and portion 119; and image light 136 may be departing, transmitted, or reflected light from stage 106 or portion 119, and transmitted to or incident upon splitter 108 and camera 104. Imaging, detection or measurement of the height (Z-value) for a point or pixel on surface 120 can be obtained by comparing the length of reference beam 5-4-6 of the optical path of the light with that of object beam 5-7-6 of the optical path. Thus, this equality of angles causes interference based on the concept of interferal metric micoscropy.

In some cases, WLI microscope 100 may include or combine an interferometer portion 119 with the optics of a microscope portion 118. In an interferometer, the interference signal of a pixel (e.g., at or upon surface 120) has maximum modulation when the optical path length of light impinging on the pixel is exactly the same for the reference beam 130 and the object beam 132. Z-value for the point on the surface (e.g., height of a pixel on surface 120; see feature (7) and D1 on surface 120 in FIG. 1B) can be obtained this way.

In some cases, microscope 100 may be an interference microscope with Mirau objective (e.g., stage 106 or portion 119). Microscope 100 may combine an interferometer with the optics of a microscope, in a setup is similar to a standard optical microscope, but includes an interferometric objective (e.g., stage 106 or portion 119) and an accurate positioning stage (e.g., Z-stage 106, which may use a piezoelectric actuator controlled by controller 116) to move the objective (e.g., lens 124 or portion 119) vertically. The reference beam 130 is reflected back in the direction of the objective front lens 124 by a beam splitter (e.g., mirror 114). On the front lens 124 there is a miniaturized mirror 122 the same size (e.g., having diameter D1) as the illuminated surface on the object (e.g., see beam 7 and D1 on surface 120 in FIG. 1B). Therefore, for high magnifications, mirror 122 is so small that its shadowing effect can be ignored. Moving the interference objective 124 (e.g., using controller 116) modifies the length of the measurement arm. The interference signal of a pixel (e.g., top of surface 120) has maximum modulation when the optical path length of light impinging on the pixel is exactly the same for the reference 130 and the object 132 beams. The z-value for the point on the surface imaged by this pixel corresponds to the z-value of the positioning stage when the modulation of the correlogram is greatest.

More specifically, FIG. 1B shows the optical path of a Mirau-interferometer. Reference beam 130 is shown by beam paths 5-4-6, and object beam 132 is shown by beam paths 5-7-6. Beam 130 and 132 have identical optical path length and can thus cause white light interference. The reference arm of microscope 100 (e.g., the Mirau interferometer) may be located within stage 106 and adjusted using controller 116. At the beam splitter 114 the source light 134 is split into a reference path (reflected) 130 and a sampling path (transmitted onto the sample) 132. On the comparison face there is a mirrored circle 122 in the middle. The two paths recombine to form an interference image (e.g., light 136). By changing the z position of the sample, such as using controller 116 top move lens 124 vertically with respect to mirror 114 and surface 120, interference images are acquired at a sequence of path (phase) differences (e.g., between length of beam 130 and 132): 0, $\lambda/4$, $\lambda/2$, and $3\lambda/4$, where $\lambda$ is the wavelength of light of beam 7, 132 or 232 (e.g., white light emitted by source 102). These interference maps are functions of background intensity, fringe modulation, and phase. Three such images provide enough information to solve for the topographic image of a sample (e.g., FIGS. 1C and 1D). In FIGS. 1A-B, microscope axis AX or beam 7 is shown parallel to or equal to an axis that is tangent to, perpendicular to, at right angles to, or bisecting surface 120—shown by tangent 121.

Figure 1C:
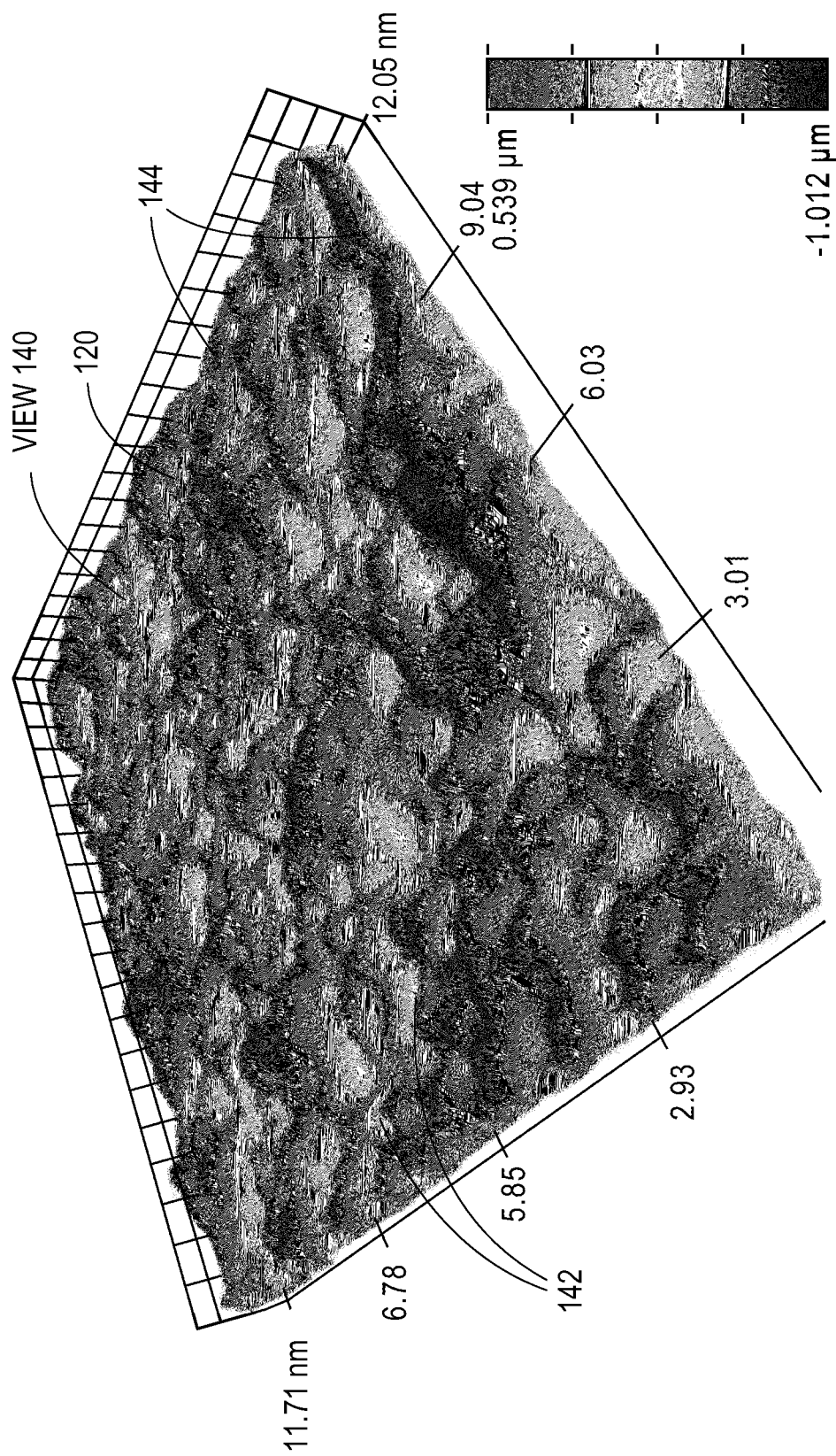
FIG. 1C is a surface profile measurement of a surface examined or detected by a WLI microscope.

FIG. 1C is a surface profile measurement of a surface examined or detected by a WLI microscope. In some cases, FIG. 1C is a surface profile measurement 140 (e.g., a 3-dimesional (3D) plan view of an image) of surface 120 examined or detected by a WLI microscope 100 (such as described for FIGS. 1A and/or 1B). In some cases, the measurement is taken without tilting as described herein. FIG. 1C may show a three-dimensional planer view 140 with lighter spots 142 indicating deeper surface position and darker spots 144 indicating higher peaks of the surface, such as in the Z-direction. FIG. 1C may include a vertical or Z resolution of 0.1 nm (e.g., $1 \times 10^{-9}$ meters) and XY resolution of 400 nm.

Figure 1D:
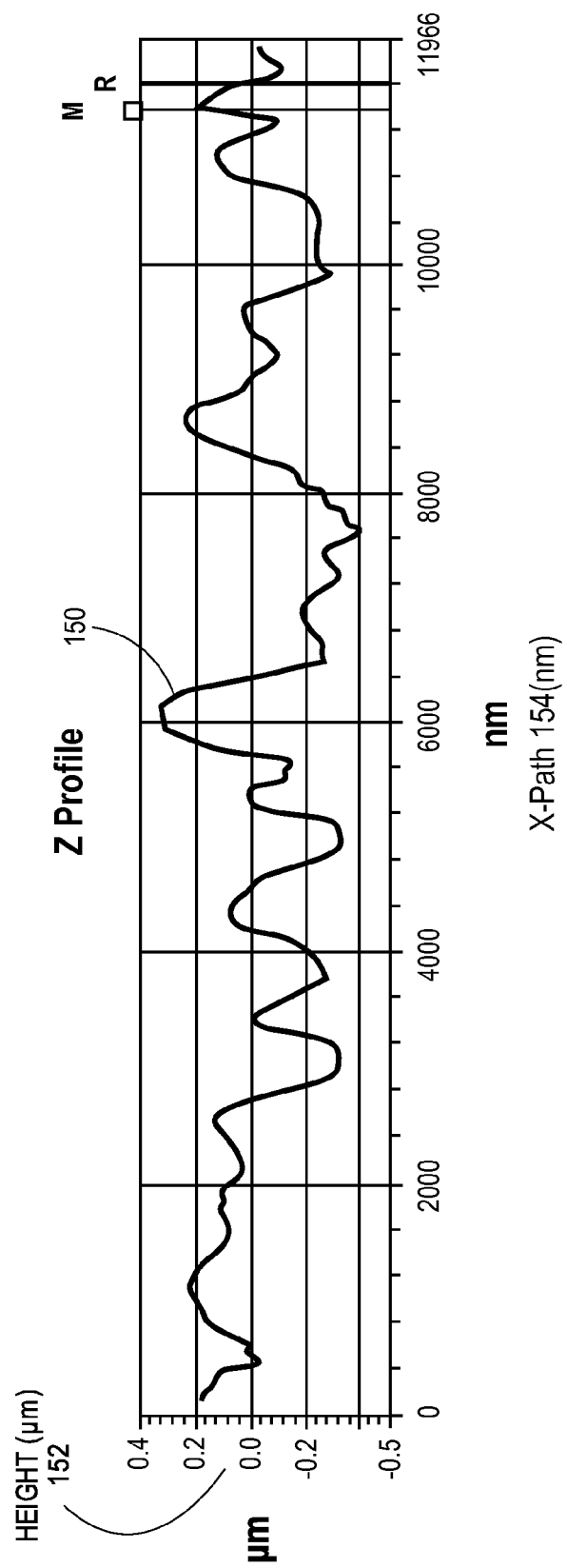
FIG. 1D is the vertical or Z-profile of the surface of the object examined by a WLI microscope.

FIG. 1D is the vertical or Z-profile of the surface of the object examined by a WLI microscope. FIG. 1D shows Z-profile 150 along X-path distance 154 of the surface 120. FIG. 1D shows Z-height amplitude 152 in micrometers versus X-path distance 154 in nanometers along the X-direction of inspection for scanning by microscope 100.

According to embodiments, microscope 100 or an "objective" of microscope 100 (e.g., Mirau objective portion (e.g., Z-stage) 106 and mirror 114; or portion 119) and or surface 120 may be tilted so that axis AX and tangent 121 are at an angle with respect to each other, as noted herein, to detect or measure dry film resist (DFR) footing defects or conductive trace undercut (CTU) defects, such as during in-line substrate package technology development (SPTD) or bump-less build-up layer (BBUL) processes.

Figure 2A:
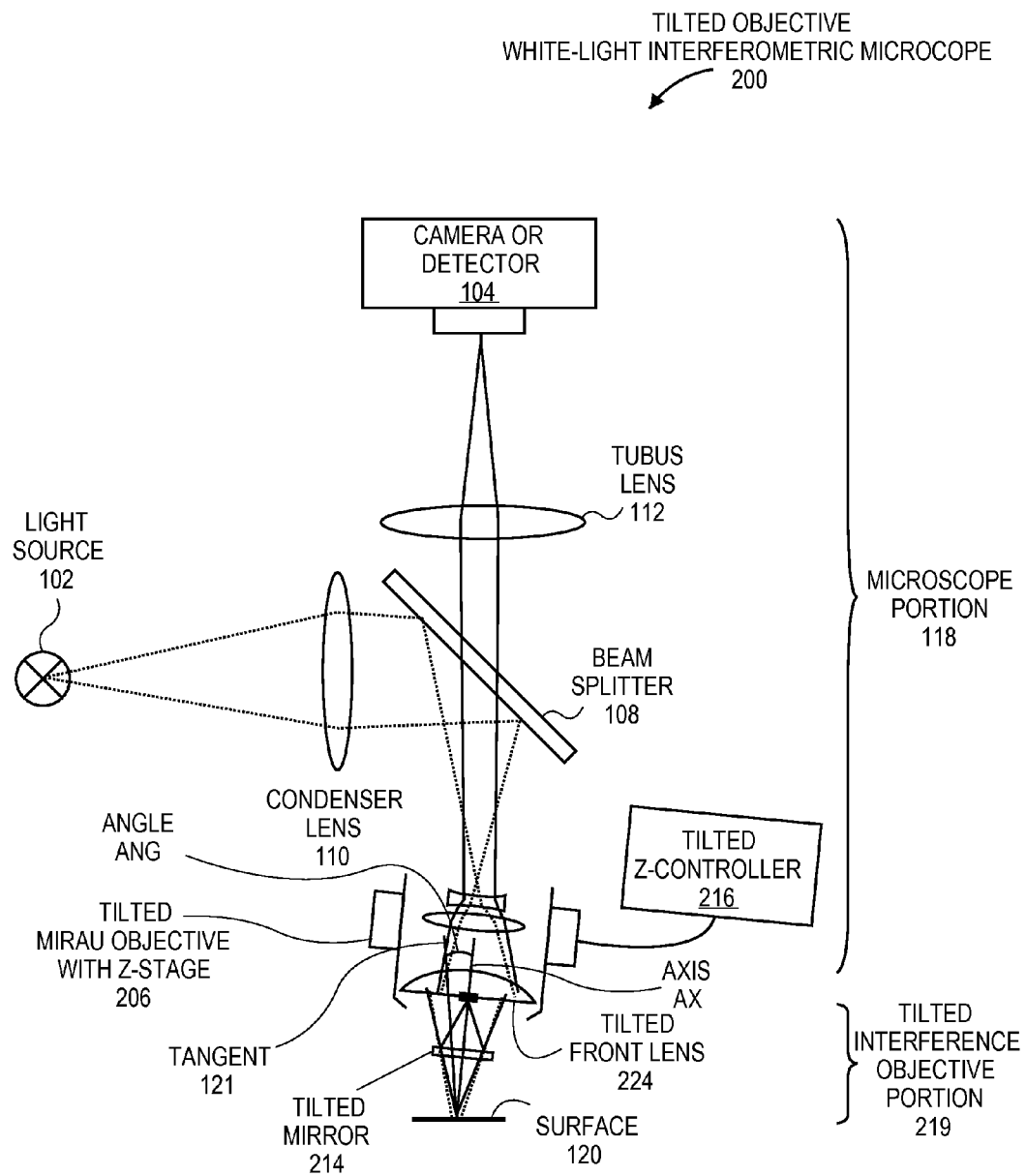
FIG. 2A is a schematic cross-sectional view of a tilted objective white-light interferometric (WLI) microscope capable of surface profile measurements using the principle of interferometry.

FIG. 2A is a schematic cross-sectional view of a tilted objective white-light interferometric (WLI) microscope capable of surface profile measurements using the principle of interferometry. FIG. 2A shows tilted WLI microscope 200 having components similar to WLI microscope 100, but having microscope axis AX or beam 7 at angel ANG (or ANG1 as noted for FIG. 5) with respect to tangent, perpendicular, bisect or right-angle of surface 120—shown by tangent 121. For instance, in some cases, lens 110 may be used or designed to focus light from the illumination source 102 onto the object lens 224, or onto surface 120 through objective 206 or portion 219. In some cases, lens 112 may be used or designed to converge parallel light to form images, such as by converging or focusing onto detector 104 light received from object lens 224, or from surface 120 through objective 206 or portion 219.

Here, the light from source 102 is also split by splitter 108 towards tilted Mirau objective with Z-stage 206, for illuminating surface to be examined 120 through tilted mirror 214. Tilted Mirau objective with Z-stage 206 includes tilted Z-controller 216 for controlling Z height of Z-stage 206 (e.g., tilted lens 224). In some cases, surface to be examined 120 is or includes a surface of a substrate (e.g., surface 305 substrate 304 described below) having DFR (e.g., islands 322 described below) or conductive traces (e.g., traces 324 described below); or a surface of a platform to hold such a substrate (e.g., a platform upon which substrate 300, or a substrate including insulating layer 304, islands 322 or traces 324 is disposed or mounted).

Figure 2B:
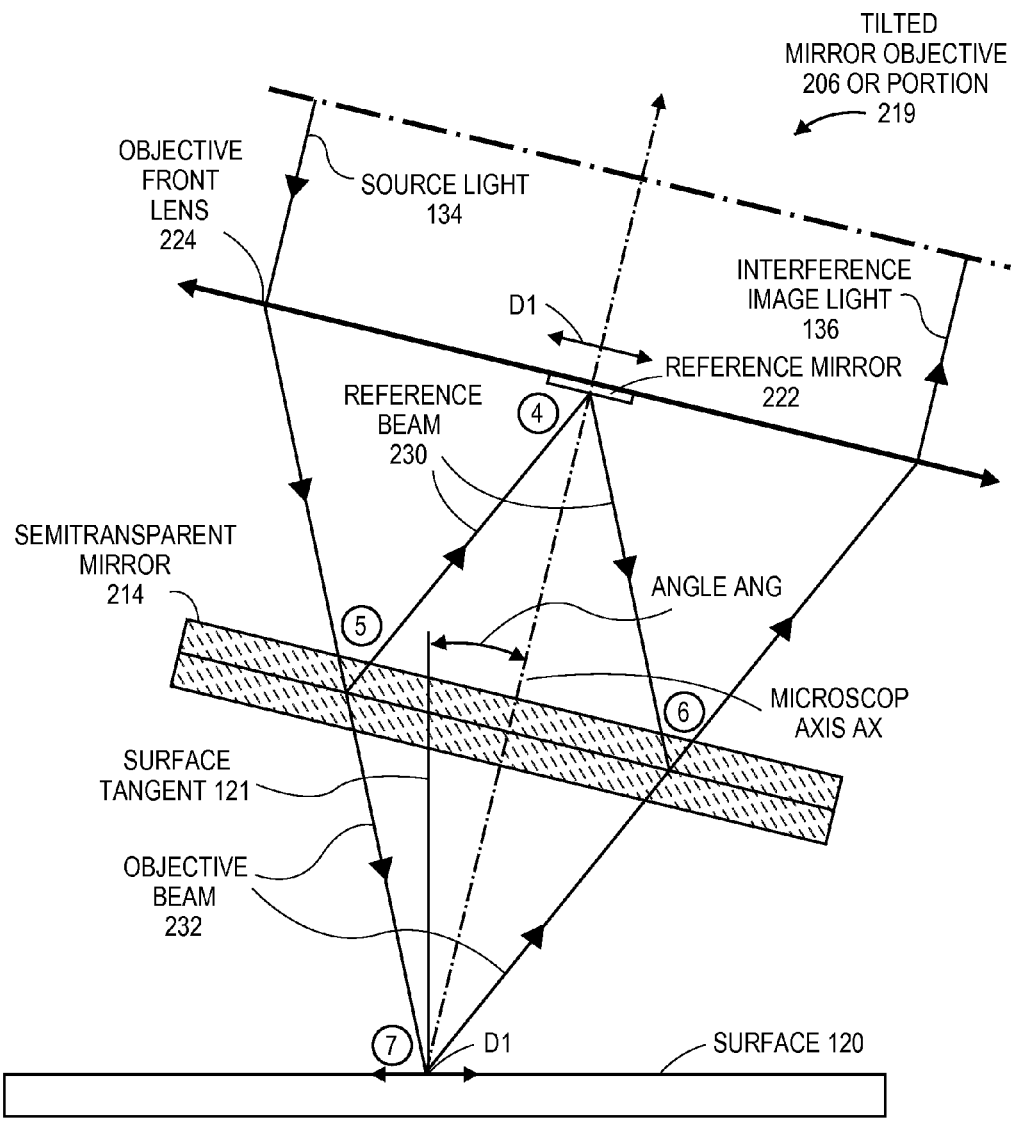
FIG. 2B is a schematic cross-sectional schematic diagram of a tilted Mirau objective portion of a WLI microscope.

FIG. 2B is a schematic cross-sectional schematic diagram of a tilted Mirau objective portion 219 of microscope 200. Tilted Mirau objective portion 219 includes tilted objective or front lens 224 of the microscope, tilted semitransparent mirror 214, tilted reference mirror 222 (mounted on bottom surface of lens 224) with tilted reference beam 230, first reflection of reference beam (5), third reflection of reference beam (6), and reflection of object beam (7). It may or may not include surface 120.

In FIG. 2B, shows microscope axis AX or beam 7 at angel ANG (or ANG1 as noted for FIG. 5) with respect to tangent, perpendicular, bisect or right-angle of surface 120—shown by tangent 121. FIG. 2B shows portion 219 having reflections or light beams 1, 2, 3, 4, 5, 6 and 7. Source light 134 may be incident light from light source 102 and splitter 108 received from splitter 108 by Z-stage 206 and portion 219; and image light 136 may be departing, transmitted, or reflected light from stage 206 or portion 219, and transmitted to or incident upon splitter 108 and camera or detector 104. Imaging, detection or measurement of the height (Z-value) for a point or pixel on surface 120 can be obtained by comparing the length of reference beam 5-4-6 of the optical path of the light with that of object beam 5-7-6 of the optical path. Thus, this equality of angles causes interference based on the concept of interferal metric micoscropy, such as described above for FIG. 1B.

According to some embodiments, the objective lens if microscope 200 can be tilted in a microscope or by as process as known in the art. In some cases, in FIGS. 2A-B, the angle of incident light into and light exiting the objective 206 or lens 224 may be vertical. In some cases it may be tilted at angel ANG (or ANG1). For example, in FIG. 2B the angle of source light 134 is incident at angle ANG, and image light 136 exits at angle ANG. However, in other cases, the angle of source light 134 may be incident vertically (e.g., at tangent 121) and bent or converted to angle ANG (e.g., for beams 230 and 232) by or below lens 224, and image light 136 may exit vertically (e.g., at tangent 121) and have been bent or converted to vertical from angle ANG (e.g., for beams 230 and 232) by or below lens 224. According to some embodiments, microscope with a tilted objective lens can be provided as know in the art.

FIGS. 3A-3E may describe the process flow in SPTD and illustrate how DFR footing and CTU defects (e.g., "hidden defects") are formed. For simplicity, some processes such as electro-less plating, etching, and Czochralski (CZ) crystal growth may not be discussed here. However, due to angle ANG (or ANG1 as noted for FIG. 5) achieved as explained for embodiments described herein, it is possible to measure, image or detect dry film resist (DFR) footing or conductive trace undercut (CTU) defects, such as by (1) imaging the base or interface of islands 322 at surface 305 of substrate 304 as described below and/or (2) imaging the base or interface of traces 324 at surface 305 of substrate 304 as described below, such as during in-line substrate package technology development (SPTD) or bump-less build-up layer (BBUL) processes (e.g., see FIGS. 3-6).

Figure 3A:
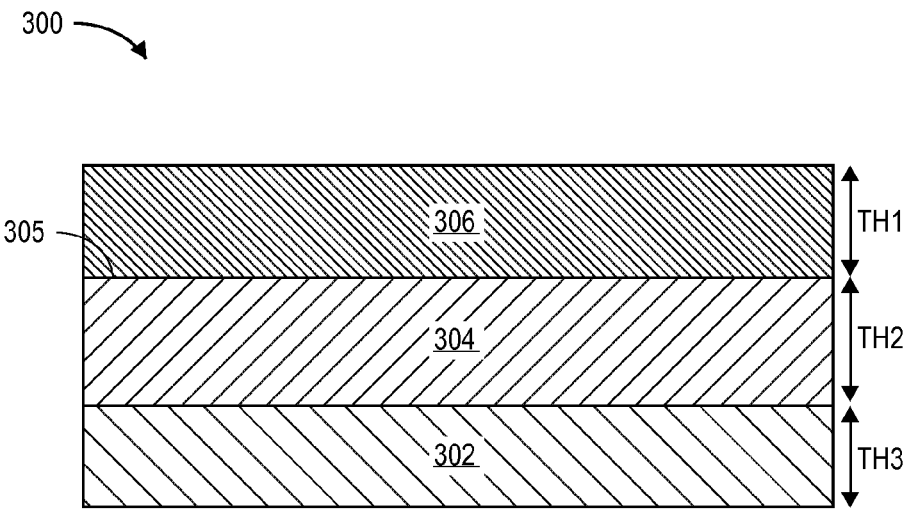
FIG. 3A is a schematic cross-sectional view of a portion of a substrate having a substrate surface upon which conductive traces will be formed.

FIG. 3A is a schematic cross-sectional view of a portion of a substrate having a substrate surface upon which conductive traces will be formed. FIG. 3A shows a portion of substrate 300 having substrate surface 305 upon which conductive traces will be formed. FIG. 3A shows substrate 300 having resist layer 306 laminated, coated or formed on the insulating substrate top surface 305 of insulating substrate layer 304, which is laminated or formed on the top surface of conductor layer 302. In some cases, FIG. 3A includes laminating a layer of DFR (e.g., layer 306) on an ABF surface (e.g., surface 305).

Resist layer 306 may be or include a dry film resist (DFR) material, a photo resist material, an acrylic based polymer material, an visually clear material, a material that is known for use as a resist layer when forming electronic device packages or use as a resist layer used in lithographic patterning to form conductive traces (e.g., traces 324 below). Resist layer 306 may be formed on surface 305 by a process, such as is known for resists used in lithographic patterning to form conductive traces. Layer 306 may have thickness TH1 between 5 and 30 microns (e.g., 1×10-6 meters). In some cases, layer 306 may have thickness TH1 between 10 and 15 microns.

Layer 304 may be an insulating substrate, a microprocessor packaging substrate, or a substrate having a surface of dielectric, insulator, or ajinomoto build-up film (ABF). Layer 304 may be or include an insulating substrate, a dielectric material, an electrically insulating material, a polymer material, a polymer material with SiO2 filler, an epoxy with filler (e.g., SiO2), an epoxy without filler, a printed circuit board material, or a material that is known for use as an insulating substrate layer of electronic device packages or use as a layer upon which perform lithographic patterning to form conductive traces (e.g., traces 324 below). Layer 304 may be formed on the top surface of layer 302 by a process, such as is known for forming insulating substrate layers used in electronic device packages or used in lithographic patterning to form conductive traces. Layer 304 may have thickness TH2 between 5 and 30 microns. In some cases, layer 306 may have thickness TH2 between 10 and 15 microns.

Layer 302 may be or include a conductor layer, a conductive material, a layer of conductive material, a metal, an alloy, copper (Cu), or a material that is know for use as a conductor or a conductive layer in electronic device packages or microprocessor packaging. Layer 306 may be formed by a process, such as is known for forming conductive layers used in electronic device packages. Layer 302 may have thickness TH3 between 5 and 30 microns. In some cases, layer 306 may have thickness TH3 between 10 and 15 microns. Layer 302 may be a metal or conductor, such as copper, gold or aluminum.

Figure 3B:
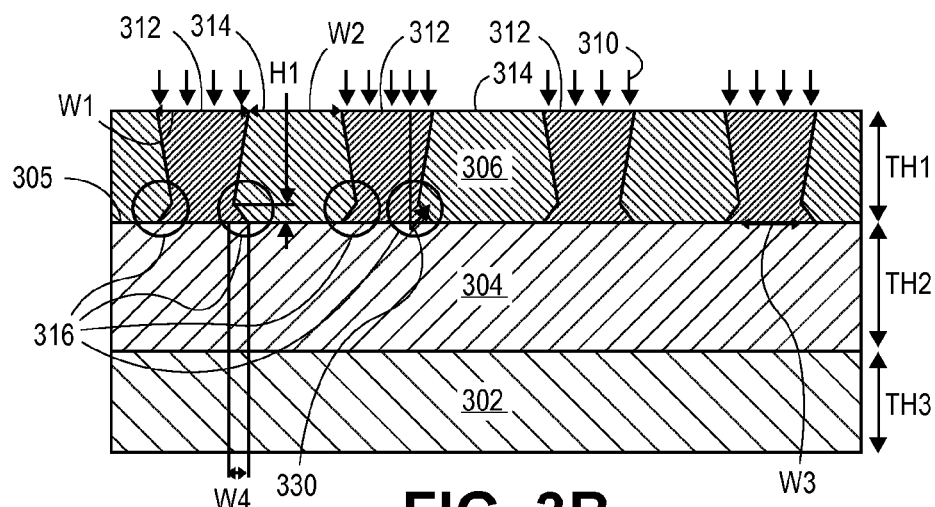
FIG. 3B shows the substrate of FIG. 3A, after exposing areas of the top surface of the resist layer to light so that portion of the resist layer can be removed where conductive traces are desired to be formed on the surface of the insulating layer.

FIG. 3B shows the substrate of FIG. 3A, after exposing areas of the top surface of the resist layer to light so that portion of the resist layer can be removed where conductive traces are desired to be formed on the surface of the insulating layer. FIG. 3B shows substrate 300, after exposing areas 312 of the top surface of the resist layer 306 to light so that portion of resist layer 306 can be removed where conductive traces (e.g., 324) are desired to be formed on the surface 305.

FIG. 3B shows areas 312 exposed to light, such as by forming a mask on areas 314 so that areas 314 are not exposed to a light incident upon a top surface of layer 306. In some cases, FIG. 3B includes exposing areas 312 of a layer of DFR (e.g., layer 306) to ultraviolet light using photo lithography, such by placing a mask with openings corresponding to areas 312 above or over layer 306, and exposing the mask and layer 306 to the light. Thus, areas 312 are exposed to the light and will harden, be cured, be developed, or undergo chemical reaction or change so that unexposed areas 314 can be patterned or dissolved while areas 312 remain.

Areas 312 have width W1 and areas 314 have width W2. It can be appreciated that areas 314 may have a length into the page, such as appropriate for a conductive trace formed on the top surface 305 of layer 304. Similarly, areas 312 may have a length into the page similar to areas 314. In some cases, areas 312 may have a length into the page as appropriate for a resist "islands" between which conductive traces will be formed on the top surface 305 of layer 304.

Light 310 may be used to expose areas 312 and may form direct exposed footing 315 having width W3. Light 310 used to expose areas 312 and may reflect off the top surface 305 of layer 304, as shown by light reflection from insulating substrate interface 330. The reflected light may form reflective exposed resist layer 306 footing defects 316 (e.g., of reflectively exposed resist). Footing defects 316 may have height H1 adjacent to direct exposed footing 315. Footing defects 316 may have width W4 adjacent to direct exposed footing 315 having width W3. Width W4 may be defined from the extension of the angle of sidewall 323 of islands 322 where those sidewalls intersect the top surface 305 of layer 304.

In some cases, FIG. 3B includes exposing more DFR at the interface (e.g., surface 305) and thus forming DFR footings 316 of exposed resist due to light reflection 330 at an DFR/ABF interface (e.g., surface 305). The total width of the exposed "island" base may be W3 plus 2×W4. In some cases, height H1 may be between 1 and 5 microns. In some cases, width W4 may be between 1 and 5 microns.

Figure 3C:
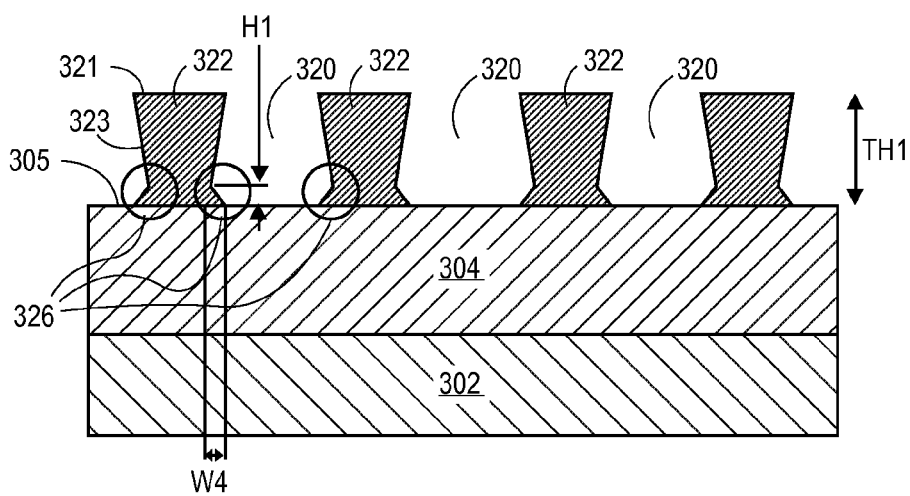
FIG. 3C shows the substrate of FIG. 3A after removing the portions of the resist layer that were not exposed to light in FIG. 3B to form openings in the resist layer where conductive traces are desired to be formed on the surface of the insulating substrate.

FIG. 3C shows the substrate of FIG. 3A after removing the portions of the resist layer that were not exposed to light in FIG. 3B to form openings in the resist layer where conductive traces are desired to be formed on the surface of the insulating substrate. FIG. 3C shows substrate 300 after removing the portions of resist layer 306 under areas 314 that were not exposed to light 310 to form openings 320 in resist layer 306 where conductive traces are desired to be formed surface 305.

FIG. 3C may include patterning or removing the un-exposed resist layer 306 in areas 314 after developing the exposed resist in areas 312, thus exposing surface 305, resist island sidewalls 323, and resist footing defects 326. Defects 326 may be or may be remaining resist from exposed film defects 316 in areas 314 that were formed by light reflection from insulating substrate interface 330. In some cases, FIG. 3C includes patterning the un-exposed DFR after developing the exposed DFR, to remove layer 306 and expose surface 305 and defects 326 (e.g., exposed film defects 316) in areas 314.

FIG. 3C shows DFR islands 322 under areas 312 and between openings 320 forms under areas 314. Islands 322 have top surface 221, height TH1, sidewalls 323 and resist footings 326. FIG. 3C may include "developing" or "patterning" resist layer 306 material to remove resist layer 306 material from below areas 314. It can be appreciated that islands 322 may have width W1, height H1 and a length into the page, such as appropriate for a resist "islands" between which conductive traces will be formed on the top surface 305 of layer 304.

Figure 3D:
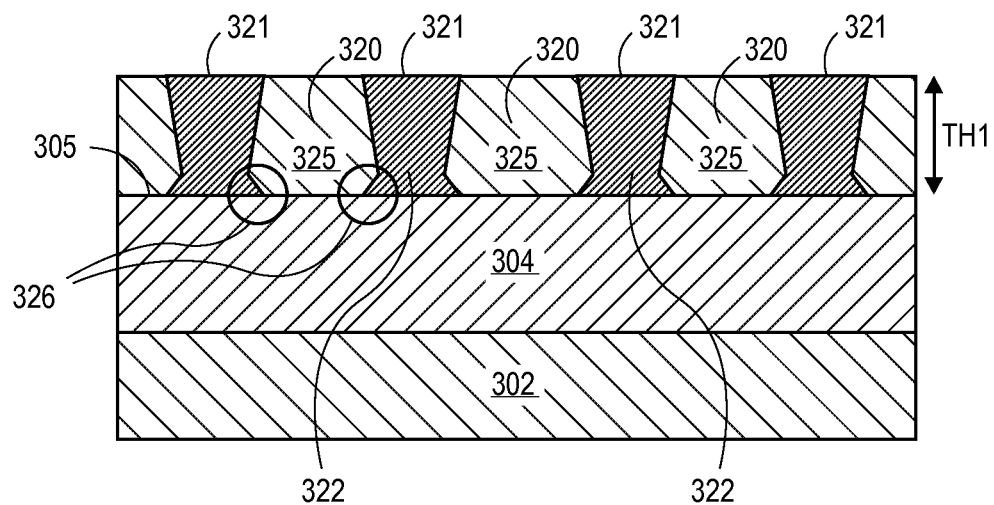
FIG. 3D shows the substrate of FIG. 3A after plating the openings where conductive traces are desired to be formed on the surface of the insulating substrate with conductor.

FIG. 3D shows the substrate of FIG. 3A after plating the openings where conductive traces are desired to be formed on the surface of the insulating substrate with conductor. FIG. 3D shows substrate 300 after plating the openings 320 where conductive traces are desired to be formed on surface 305 with conductor 325. Conductor 225 may be the material that forms traces 224. Conductor 325 may be a conductor as described above for layer 302. In some cases, FIG. 3D includes patterning Copper traces on openings 320 where the un-exposed DFR has been removed and surface 305 is exposed in areas 314.

In some cases FIG. 3D shows conductive plating 325 formed in openings 320. Forming plating 325 may include electro-less plating on the top surface 305 of layer 304 and sidewalls 323 of islands 322, prior to direct conductive plating and openings 320. Forming plating 325 may also include planarizing the material and plating 325 down to height TH1 or the top surface 321 of islands 322.

Figure 3E:
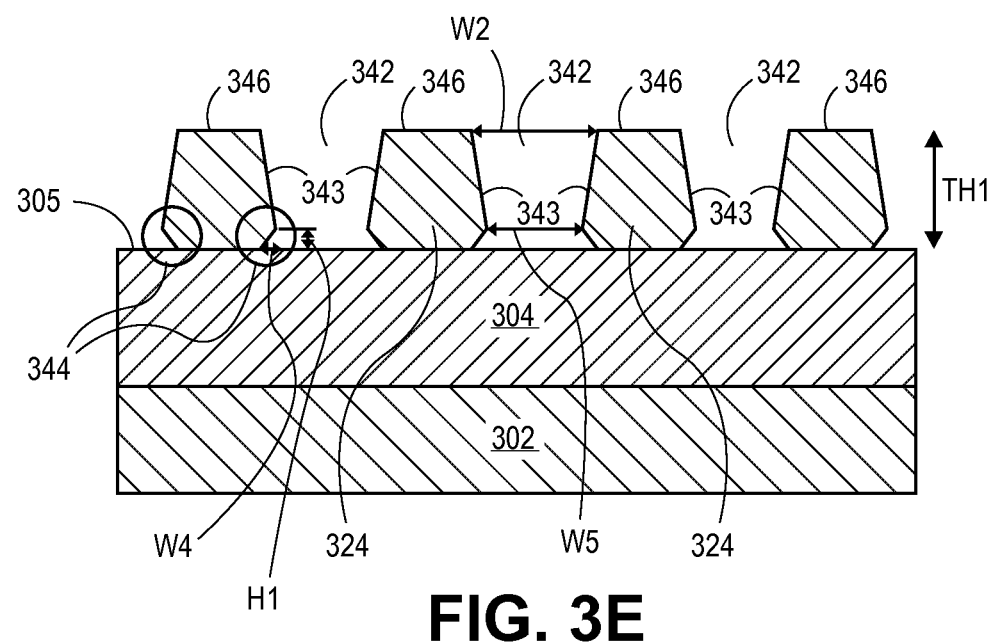
FIG. 3E shows the substrate of FIG. 3A after polishing the conductor, and etching to remove the resist layer between the conductive traces.

FIG. 3E shows the substrate of FIG. 3A after polishing the conductor, and etching to remove the resist layer between the conductive traces. FIG. 3E shows the substrate 300 after polishing the conductor plating 325 (e.g., as described above), and etching to remove the resist layer islands 322 from between the conductor plating 325 to form conductive traces 324 having sidewalls 343 and top surfaces 346.

FIG. 3E may show the substrate of FIG. 3A after polishing the conductor, and etching to remove the resist layer between the conductive traces. shows conductive traces 324 after removing islands 322 from the top surface of layer 305. Removing the islands may include etching as know in the art to remove the exposed resist islands 322 to form openings 342 between traces 324. In some cases, removing the islands may include etching away the resist film using a wet chemical etching process. During this process, strip solution is sprayed on the resist film, and resist film is broken into particles through chemical reactions. Traces 324 are shown having height TH1 and conductive trace undercut defects 344. Undercut defects 344 may be caused by or result from the existence of footing defects 316. For example, removal or etching of islands 322 may include removal or etching of footings 316, thus leaving open footing defects 344 within openings 342. Undercuts 344 may have a dimension similar to the inversion or opposite of footings 326. Openings 342 may have width W2 at their top, which is adjacent surfaces 346; width W5 at their closest point, which is above undercuts 344; and width W5 plus 2×W3 at their base. Undercuts 344 may have width W4 and height H1. Width W4 may be defined from the extension of the angle of sidewall 323 of islands 322, and/or from sidewall 343 of traces 324, where those sidewalls intersect the top surface 305 of layer 304.

As can be seen, larger DFR footing defects 326 may results in larger CTU defects 344, and larger CTU defects may results in smaller contact area between traces 324 and surface 305 of layer 304, thus increasing the risk of traces 324 lifting off of, or becoming detached (partially or wholly) from surface 305. Such liftoff can result in damaged, destroyed or missing lengths of the conductive traces, often causing undesired open circuits in the trace circuitry.

Embodiments described herein, provide devices and processes for using a microscope with a tilted objective lens to provide a high-throughput and low cost metrology and tool for non-destructive, non-contact in-line monitoring (e.g., inspection, imaging and/or detection) of both resist footing defects (e.g., after Figure C) and conductive trace undercut defects (e.g., after Figure E). Such in-line inspection may inspect for dry film resist (DFR) footing and conductive trace undercut (CUT) defects in the plating interface, edge or bonding between the conductive trace base or plating bottom, and insulating substrate top surfaces (e.g., for hidden defects such as the footing and undercut defects) using a white light interferometer microscope with a tilted objective lens (and/or a tilted microscope or substrate platform).

According to some embodiments, all of microscope 100 (e.g., portion 118 and 119 of FIG. 1A-B), or an "objective" of microscope 100 (e.g., Mirau objective portion 106 and mirror 114; or portion 119; such as shown by stage 206, mirror 214, or portion 219 of FIG. 2A-B) and/or surface 120 may be tilted to put axis AX at angles ANG and ANG1 (e.g., see FIG. 4) or ANG1 (e.g., see FIG. 5) with respect to tangent 121, such as to detect or measure dry film resist (DFR) footing defects or conductive trace undercut (CTU) defects, such as during in-line substrate package technology development (SPTD) or bump-less build-up layer (BBUL) processes.

Figure 6:
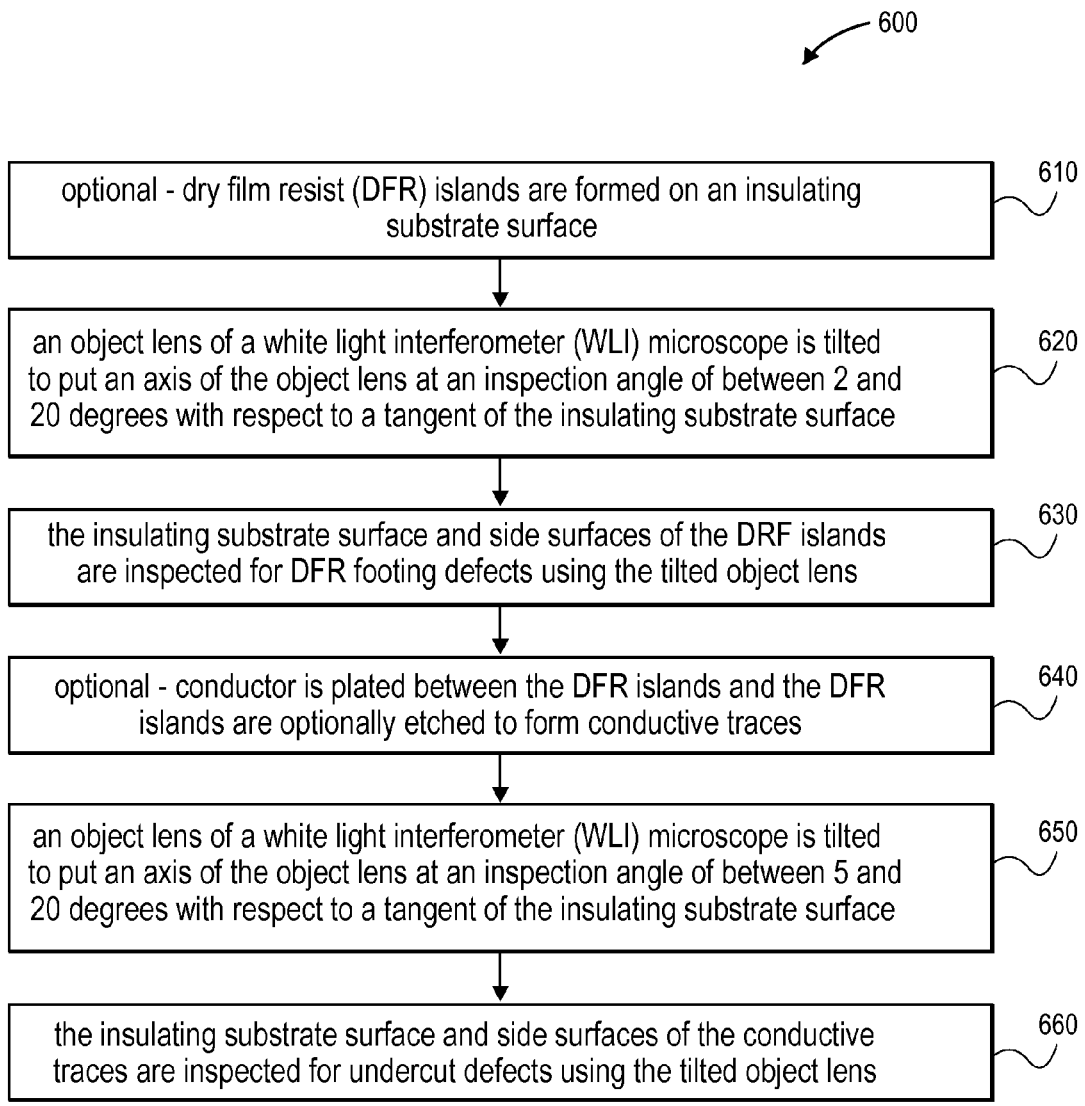
FIG. 6 is a flow diagram of an in-line process for detecting resist island footing defects and conductive trace undercut defects at an interface between the defects and an insulating substrate surface.

As shown in FIGS. 4-6, setups (e.g., setups 402 and 502) can include a WLI microscope with an objective lens tilted to an appropriate angle so that hidden areas (e.g., footings 326 and undercut 344) which can not be imaged using traditional WLI setup (e.g., setup 401) can be reached by the microscope beam (e.g., beam 7 or 232). As a comparison, without tilting the lens, the footings and undercuts are shadowed by the top surface of DFR, or sidewalls of the traces, and therefore, a corresponding surface profile or image will not reflect the hidden areas (e.g., footing or undercut signature). On the other hand, when an object lens is tilted to an optimized angle, the microscope beam is able to scan the footing and undercut areas and measurement of footing and undercut profiles and dimensions can be achieved by analyzing the surface profiles.

In some cases, to image undercut defects, a larger tilting angle might be needed, which can be achieved by tilting both the objective lens and the substrate (e.g., surface 120) if needed. Furthermore, embodiments include rotating the objective lens from zero to 360 degrees, such as by rotating microscope 200 or the tilted objective lens around tangent 121, so that the footings and undercuts can be viewed at different angles.

For some embodiments, experimental trials successfully demonstrated that DFR footing and CTU could be imaged using WLI with a tilted objective lens. The dimension measured using this WLI was consistent with the result from tradition physical cross-sections taken to detect footings and undercut. Also, a Z resolution of 0.1 nm and XY resolution of 400 nm were achieved. For some embodiments, experimental trials had an overall time for tool (WLI with a tilted objective lens) setup and measurement (detect footings and undercut) of less than 1 min, while tradition cross-section and imaging of the same detect footings and undercut required 2 hours. With such embodiments, immediate feedback of detect footings and undercut can be provided to improve package fabrications processes and processing, and yield loss and product development cycle can be reduced.

Specifically, according to embodiments, it is possible to measure, image or detect dry film resist (DFR) footing defects 326 and conductive trace undercut (CTU) defects 344 by (1) imaging the base or interface of islands 322 at surface 305 of substrate 304 (e.g., at FIG. 3C); and (2) imaging the base or interface of traces 324 at surface 305 of substrate 304 (e.g., at FIG. 3E), by tilting or using tilted (1) surface 120 and/or (2) microscope 100 or an "objective" of microscope 100, to put axis AX at angles ANG and ANG1 with respect to tangent 121, such as during in-line substrate package technology development (SPTD) or bump-less build-up layer (BBUL) processes (e.g., see FIGS. 4-6). As noted above, this may include tilting all of microscope 100 (e.g., portion 118 and 119 of FIG. 1A-B), or an "objective" of microscope 100 (e.g., stage 206, mirror 214, or portion 219 of FIG. 2A-B) to put axis AX at angles ANG and ANG1 with respect to tangent 121.

FIG. 4A shows an inspection setup for inspecting the top surface of the insulating substrate, the side surface of the resist islands, and the top surface of the resist islands of FIG. 3C to detect resist islands footing defects using a WLI microscope. FIG. 4A shows monitoring, inspection, or detection setups 401 and 402 such as for detecting resist islands 322 and footing defects 326 of islands 322. More specifically, FIG. 4A shows an inspection setup 401 and setup 402 for inspecting the top surface 305 of the insulating substrate, the side surfaces 406 (e.g., sidewalls 323 and footings 326) of the resist islands, and the top surface 321 of the resist islands of FIG. 3C to detect resist islands footing defects 326. This inspecting may occur during in-line formation of a processor package, such as by inspecting for the footings after forming the DFR islands and prior to forming or plating conductor between the islands. This inspecting may include creating a three-dimensional X,Y surface profile image having a Z resolution between 1 and 2 nm of the insulating substrate surface and DFR island sidewalls. This inspecting may include imaging at a Z-resolution capable of imaging a DFR footing defect height of between 200 nm and 2 microns (or 1-5 microns); and a width of between 200 nm and 2 microns (or 1-5 microns).

Setup 401 may be or include using microscope 100 having axis AX equal to tangent 121 (e.g., microscope 100 at a vertical angle) inspecting top surface 305, side surface 406 and top surfaces 321 of island 322 at vertical angles 405. Angles 405 may be based on or equal to axis AX or beam 7. Inspection using setup 401 may provide surface profile 410, such as shown in FIG. 4B.

For instance, FIG. 4B shows a surface profile using a WLI microscope at a vertical or 90 degree angle, with respect to a top surface of the FIG. 4A surface 305. In some cases, FIG. 4B shows surface profile 410, such as obtained when monitoring, inspecting, or detecting for footing defects 326 using a WLI microscope (e.g., microscope 100) at a vertical or 90 degree angle, with respect to a top surface of the FIG. 4A surface 305. In some cases, inspection using microscope 100 provides surface profile 410. Surface profile 410 is shown including portion 415 as images of surface 305, portion 423 as images of side surface 406, portion 421 as images of surface 321 and corners 416 as images of footings 326.

Due to the vertical nature of setup 401, portion 423 is not able to image the actual sidewalls 323 or footings 326 because angles 405 are (optically) blocked by top surface 321 of islands 322. Thus, profile 410 does not detect sidewalls 323 or footing defects 326. More specifically, corners 416 do not image, detect or identify resist island 322 footings defects 326 because angles 405 are optically blocked by top surface 321 of islands 322. Thus, profile 410 does not detect sidewalls 323 or footing defects 326. Here footing 326 is a "hidden defect".

Setup 402 may be or include tilting or using tilted (1) surface 120 and/or (2) microscope 100 or an "objective" of microscope 100, to put axis AX at angle ANG with respect to tangent 121 to inspect (and optionally inspecting) top surface 305, side surface 406 (e.g., sidewalls 323 and footings 326) and top surfaces 321 of island 322 at angles ANG. Angles ANG may be based on or equal to the difference between axis AX and tangent 121. According to embodiments, angle ANG may be an inspection angle of between 2 and 20 degrees. In some cases, angle ANG is between 2 and 10 degrees. In some cases, angle ANG is between 2 and 5 degrees. In some cases, angle ANG is 3 degrees. Inspection using setup 402 and/or angle ANG may provide surface profile 420, such as shown in FIG. 4C.

For instance, FIG. 4C shows a surface profile using a tilted WLI microscope (e.g., microscope 200) (and/or tilted surface 120) at a non-vertical or angle of between 70 and 88 degree with respect to a top surface of the FIG. 4A surface 305. In some cases, FIG. 4C shows surface profile 320, such as obtained when monitoring, inspecting, or detecting for footing defects 326 using tilted microscope 100 or a tilted "objective" of microscope 100 (e.g., microscope 200), to put axis AX at angle ANG of between 2 and 20 degrees with respect to tangent 121. In some cases, inspection using microscope 200 provides surface profile 420. Surface profile 420 is shown including portion 435 as images of surface 305, portion 433 and 434 as images of side surface 406 (e.g., including sidewalls 323 and footing 326), portion 431 as images of surface 321, and corners 436 as images of footings 326.

Due to tilting or using tilted (1) surface 120 and/or (2) microscope 100 or an "objective" of microscope 100 (e.g., microscope 200), to put axis AX at angle ANG of between 2 and 20 degrees with respect to tangent 121, portion 433 is not able to image the actual sidewalls 323 or footings 326 because angles 405 are (optically) blocked by top surface 321 from imaging footings 326.

However, (possibly unexpectedly advantageous) due to tilting or using tilted (1) surface 120 and/or (2) microscope 100 or an "objective" of microscope 100 (e.g., microscope 200), to put axis AX at angle ANG of between 2 and 20 degrees with respect to tangent 121, portion 434 is able to image the actual sidewalls 323 and footings 326 because angles ANG are (optically) not blocked by top surface 321 of islands 322. Here, due to imaging with axis AX or beam 7 at angle ANG, the microscope or imager is able to penetrate in the horizontal direction to detect or image walls 323 and footing defects 326 in portion 434. Thus, profile 420 does detect sidewalls 323 or footing defects 326. More specifically, corners 436 do image, detect or identify resist island 322 footings defects 326 because angles 406 are optically not blocked by top surface 321 of islands 322 for portion 436. Thus, profile 420 does detect sidewalls 323 or footing defects 326.

It can be appreciated that rotating setup 402 by 180 degrees with respect to the vertical axis (e.g., tangent 121) allows footing defect 326 to be detected or imaged for portion 433 (but, then, not for portion 434). It is considered that setup 402 can be rotated by various degrees (e.g., 30, 45, 60, 90, 120, 150, 180, 270, etc.) with respect to the vertical axis (e.g., tangent 121) to allow footing defects (e.g., such as defect 326) to be detected or imaged for various side surface portions (e.g., similar to imaging of portion 434 to detect sidewalls 323 and footings 326).

FIG. 5A shows an inspection set up for inspecting the top surface of the insulating substrate, the side surface of the conductive trace, and the top surface of the conductive trace of FIG. 3E to detect conductor trace undercut (CUT) defects using a WLI microscope. FIG. 5A shows monitoring, inspection, or detection setups 401 and 502 such as for detecting the conductive traces 324 and undercut defects 344 of traces 324. More specifically, FIG. 5A shows an inspection setup 401 and setup 502 for inspecting the top surface 305 of the insulating substrate, the side surfaces 506 (e.g., sidewalls 343 and undercut 344) of the conductive trace, and the top surface 346 of the conductive trace of FIG. 3E to detect undercut defects 344. This inspecting may occur during in-line formation of a processor package, such as by inspecting for the undercuts, after formation of the conductive traces, and prior to forming a material over or on the copper traces. This inspecting may include creating a three-dimensional X,Y surface profile image having a Z resolution between 1 and 2 nm of the insulating substrate surface and copper trace sidewalls. This inspecting may include imaging at a Z-resolution capable of imaging an undercut defect height of between 200 nm and 2 microns (or 1-5 microns); and a width of between 200 nm and 2 microns (or 1-5 microns).

Setup 501 may be or include using microscope 100 having axis AX equal to tangent 121 (e.g., microscope 100 at a vertical angle) inspecting top surface 305, side surface 506 and top surfaces 346 at vertical angles 405. Inspection using setup 401 may provide surface profile 510, such as shown in FIG. 5B.

For instance, FIG. 5B shows a surface profile using a WLI microscope at a vertical or 90 degree angle, with respect to a top surface of the FIG. 5A surface 305. In some cases, FIG. 5B shows surface profile 510, such as obtained when monitoring, inspecting, or detecting for undercut defects 344 using a WLI microscope (e.g., microscope 100) at a vertical or 90 degree angle, with respect to a top surface of the FIG. 5A surface 305. In some cases, inspection using microscope 100 provides surface profile 510. Surface profile 510 is shown including portion 515 as images of surface 305, portion 523 as images of side surface 506, portion 521 as images of surface 346 and corners 516 as images of undercuts 344.

Due to the vertical nature of setup 401, portion 523 is not able to image the actual undercuts 344 because angles 405 are (optically) blocked by sidewalls 343. Thus, profile 510 does not detect undercuts or CUT defects 344. More specifically, corners 516 do not image, detect or identify defects 344 because angles 405 are optically blocked by sidewalls 343. Thus, profile 510 does not detect defects 344. Here the undercut defect is a "hidden defect."

Setup 502 may be or include tilting or using tilted (1) surface 120 and/or (2) microscope 100 or an "objective" of microscope 100 (e.g., microscope 200), to put axis AX at angle ANG1 with respect to tangent 121 to inspect (and optionally inspecting) top surface 305, side surface 506 (e.g., sidewalls 343 and undercuts 344) and top surfaces 346 at angles ANG1. Angles ANG1 may be based on or equal to the difference between axis AX and tangent 121. According to embodiments, angle ANG1 may be an inspection angle of between 5 and 20 degrees. In some cases, angle ANG1 is between 5 and 15 or 5 and 10 degrees. In some cases, angle ANG1 is between 8 and 12 degrees. In some cases, angle ANG1 is 10 degrees. In some cases, obtaining ANG1 includes tilting both the objective lens and surface 120. Inspection using setup 502 and/or angle ANG1 may provide surface profile 520, such as shown in FIG. 5C.

For instance, FIG. 5C shows a surface profile using a tilted (1) surface 120 and (2) microscope 100 or an "objective" of microscope 100 (e.g., microscope 200) at a non-vertical or angle of between 70 and 85 degrees with respect to a top surface of the FIG. 5A surface 305. In some cases, FIG. 5C shows surface profile 520, such as obtained when monitoring, inspecting, or detecting for undercut defects 344 using tilted microscope 100 or a tilted "objective" of microscope 100 (e.g., microscope 200), to put axis AX at angle ANG1 of between 5 and 20 degrees with respect to tangent 121. In some cases, inspection using microscope 200 provides surface profile 520. Surface profile 520 is shown including portion 535 as images of surface 305, portion 533 and 534 as images of side surface 506 (e.g., including sidewalls 343 and undercut defects 344), portion 531 as images of surface 346, and corners 536 as images of undercut defects 344. Due to tilting or using tilted (1) surface 120 and/or (2) microscope 100 or an "objective" of microscope 100 (e.g., microscope 200), to put axis AX at angle ANG1 of between 5 and 20 degrees with respect to tangent 121, portion 533 is not able to image the actual sidewalls 343 or undercut defects 344 because angles 405 are (optically) blocked by sidewalls 343 from imaging undercut defects 344.

However, (possibly unexpectedly advantageous) due to tilting or using tilted (1) surface 120 and/or (2) microscope 100 or an "objective" of microscope 100 (e.g., microscope 200), to put axis AX at angle ANG1 of between 5 and 20 degrees with respect to tangent 121, portion 534 is able to image the actual undercut defects 344 because angles ANG1 are (optically) not blocked by sidewalls 343. Here, due to imaging with axis AX or beam 7 at angle ANG1, the microscope or imager is able to penetrate in the horizontal direction to detect or image sidewalls 343 and defects 344 in portion 534.

Thus, profile 520 does detect sidewalls 343 and defects 344. More specifically, corners 536 do image, detect or identify defects 344 because angles ANG1 are optically not blocked by sidewalls 343 for portion 536. Thus, profile 520 does detect sidewalls 343 or defects 344.

It can be appreciated that rotating setup 502 by 180 degrees with respect to the vertical axis (e.g., tangent 121) allows defect 344 to be detected or imaged for portion 533 (but, then, not for portion 534). It is considered that setup 502 can be rotated by various degrees (e.g., 30, 45, 60, 90, 120, 150, etc.) with respect to the vertical axis (e.g., tangent 121) to allow undercut defects (e.g., such as defect 344) to be detected or imaged for various side surface portions (e.g., similar to imaging of portion 534 to detect sidewalls 343 and undercut defects 344).

Rotating setup 402 or 502 may include rotating the microscope and/or substrate (such as by rotating a platform the substrate is disposed or mounted on). The substrate may be rotated with respect to the XY direction in order to detect defects on the opposing interface or base of the DFR or conductive trace. Similarly, the substrate may be rotated by different angles to detect defects of the DFR or conductive traces at different angles, such as to rotate to an angle tangential to, perpendicular to, bisects, or is at a right-angle to the sidewall of the DFR or conductive trace to expose the foot of the DFR or trace to detect defects if that foots interface or base.

FIG. 6 is a flow diagram of an in-line process for detecting resist island footing defects and conductive trace undercut defects at an interface between the defects and an insulating substrate surface. FIG. 6 shows in-line process 600 for inspecting, imaging, monitoring, or detecting footing defects 326 and/or for conductive trace undercut defects 344. Process 600 may include descriptions for FIGS. 4-5.

At block 610 dry film resist (DFR) islands are optionally formed on an insulating substrate surface. Block 610 may include descriptions for FIGS. 3A-3C.

At block 620 an object lens of a white light interferometer (WLI) microscope is tilted to put an axis of the object lens at an inspection angle of between 2 and 20 degrees with respect to an axis tangent to, perpendicular to, at right angles to, or bisecting the insulating substrate surface 305. Block 620 may include descriptions for FIGS. 2A-B, 3C, 4A (setup 402) and 4C.

At block 630 the insulating substrate surface and side surfaces of the DFR islands are inspected for DFR footing defects using the tilted object lens. Block 630 may include descriptions for FIGS. 2A-B, 3C, 4A (setup 402) and 4C. In some cases, inspecting at block 630 includes scanning surface 120 or 305 in a defined area such as that or a square or rectangle, and may be performed line by line in a fan beam scanning process performed by the WLI. Scanning surface 120 or 305 at block 630 may include inspecting the insulating substrate surface and side surfaces of the DFR islands by moving the insulating substrate surface with respect to the object lens, in a direction along or across (e.g., in the XY direction) the side surfaces of the DFR islands (such as using a platform).

At block 640 conductor is optionally plated between the DFR islands and the DFR islands are optionally etched to form conductive traces. Block 640 may include descriptions for FIGS. 3D-3E.

At block 650 an object lens of a white light interferometer (WLI) microscope is tilted to put an axis of the object lens at an inspection angle of between 5 and 20 degrees with respect to an axis tangent to, perpendicular to, at right angles to, or bisecting the insulating substrate surface 305. Block 650 may include descriptions for FIGS. 2A-B, 3E, 5A (setup 502) and 5C.

At block 660 the insulating substrate surface and side surfaces of the conductive traces are inspected for undercut defects using the tilted object lens. Block 660 may include descriptions for FIGS. 2A-B, 3E, 5A (setup 502) and 5C. In some cases, inspecting at block 660 includes scanning surface 120 or 305 in a defined area such as that or a square or rectangle, and may be performed line by line in a fan beam scanning process performed by the WLI. Scanning surface 120 or 305 at block 660 may include inspecting the insulating substrate surface and side surfaces of the traces by moving the insulating substrate surface with respect to the object lens, in a direction along or across (e.g., in the XY direction) the side surfaces of the traces (such as using a platform).

According to first embodiments, only blocks 620 and 630 are performed. According to second embodiments, only blocks 650 and 660 are performed. According to third embodiments, only blocks 620, 630, 650 and 660 are performed. According to fourth embodiments, any of the first through third embodiments and only one of the optional blocks are performed. According to some embodiments, any of the first through third embodiments and all of the optional blocks are performed.

According to embodiments, a white light interferometer microscope with a "tilted objective" or "tilted objective lens" is described by tilted or tilting: (1) all of microscope 100; (2) an "objective" of microscope 100; (3) Mirau objective 106 and mirror 114; (4) portion 119; and (5) optionally surface 120 so that axis AX and tangent 121 are at an angle ANG or ANG1 with respect to each other, as noted herein. According to embodiments, a white light interferometer microscope with a "tilted objective lens" is described by: (1) all of microscope 200; (2) an "objective" of microscope 200; (3) Mirau objective 206 and mirror 214; (4) portion 219; and (5) optionally surface 120 being tilted so that axis AX and tangent 121 are at an angle ANG or ANG1 with respect to each other, as noted herein.

According to other embodiments, surface 120 may be tilted (not shown but creating or adding to angle ANG) to put axis AX at angle ANG or ANG1 with respect to tangent 121, such as to detect or measure dry film resist (DFR) footing defects or conductive trace undercut (CTU) defects, such as during in-line substrate package technology development (SPTD) or bump-less build-up layer (BBUL) processes.

In some cases, both (1) surface 120 and (2) microscope 100 or an "objective" of microscope 100 may be tilted to put axis AX at angle ANG or ANG1 with respect to tangent 121, such as to detect or measure dry film resist (DFR) footing defects or conductive trace undercut (CTU) defects, such as during in-line substrate package technology development (SPTD) or bump-less build-up layer (BBUL) processes. According to some embodiments, titling both the object lens and the platform may be required for a relative angle (e.g., ANG or ANG1) of greater than 5 degrees.

Any or all of these 3 tilting embodiments may include tilting so that microscope axis AX or beam 7 is at an angles ANG and ANG1 with respect to an axis tangent to, perpendicular to, at right angles to, or bisecting the insulating substrate surface-angle 121 of surface 120, as noted herein, to image the base or interface of islands 322 at substrate 304 and/or to image the base or interface of traces 324 at substrate 304, such as during in-line substrate package technology development (SPTD) or bump-less build-up layer (BBUL) processes (e.g., see FIGS. 3-6).

In some cases, any or all of these 3 tilting embodiments may produce a surface profile measurement similar to that shown in FIG. 1C, 4C or 5C (e.g., surface profile measurement 140 of surface 120 such as described for FIGS. 2A-2B above, and/or FIGS. 4-6 below). This surface profile measurement may have a vertical or Z resolution of 0.1 nm (e.g., height resolution or detection capability of surface 120 at beam 7 or 232), and XY resolution of 400 nm (e.g., diameter D1 resolution or detection capability of surface 120 at beam 7 or 232). In some cases, any or all of these 3 tilting embodiments may produce a Z-profile of the surface of the object similar to that shown in FIG. 1D (e.g., profile 150 of surface 120 such as described for FIGS. 2A-2B above, and/or FIGS. 4-6 below). This profile measurement may have a vertical or Z resolution of 0.1 nm and XY resolution of 400 nm.

In some cases, the XY imaging resolution of the WLI microscope with tilted objective lens is between 200 nanometers and 2 microns. In some cases, the width of the dry film resist island may be between 10 and 15 microns, and the height of the dry resist film island may be 10 to 15 microns. In some cases, the defect height H1 may be between 1 and 5 microns; and defect width W4 may be between 1 and 5 microns. In some cases, the Z resolution of the image or detection using the WLI microscope with tilted objective lens may be between 1 and 5 microns. In some cases, the resolution of the image or detection with respect X,Y may be 1 to 5 microns.

In order to detecting defects in an interface between conductive traces and a insulating substrate surface, some embodiments are described as a device or system having a white light interferometer (WLI) microscope having an object lens disposed above a platform surface, where the object lens capable of being tilted at an angle to put an axis of the object lens at a first inspection angle of between 2 and 20 degrees with respect to a tangent of the platform surface. The platform surface may be configured for mounting a package substrate having dry film resist islands or conductive traces on an insulating substrate surface. In this case, a moving tool may move the platform surface laterally with respect to the microscope; and a camera may image the platform surface (or the dry film resist islands or conductive traces on an insulating substrate surface) through the microscope while moving the platform surface. The platform may be capable of being tilted at an angle to put an axis of the object lens at a first inspection angle of between 5 and 20 degrees with respect to a tangent of the platform surface.

In some cases, the WLI microscope with tilted objective lens provides advantages due to the use of white light, such as the ability to map in three dimensions with a increased resolution in the Z direction such as up to 1 nanometer of resolution; and in the X,Y direction with up to 1 micrometer of resolution. The resolution in the Z direction provides sufficient contrast and high resolution to map the defects, as noted herein. Such resolution may provide actual count, defect detection of up to 0.1 microns qualitative and quantitative.

Embodiments described herein can be used to inspect dry resist film or conductive traces formed on substrates, such as substrates used to form a microprocessor package, a "chip" package, or a printed circuit board during "in-line" processing, such as processing that does not require the substrate to be removed from a fabrication process where the substrate, or chips diced from the substrate will be manufacture for inclusion in a product; or such as without requiring the substrate to be taken from processing or tested in a laboratory (e.g. by dissection or a process that damages or causes the substrate to be unusable for sale or inclusion in a product). For example, in-line monitoring may include monitoring fabrication of devices that are sold to the public or are included in a device sold to the public. In-line monitoring may include monitoring manufacturing flow of a device or package, such as by adding the processes or embodiments described herein into the manufacturing flow, concluding manufacturing of the device, and selling the device or including the device in a product. Such in-line monitoring may occur at or after FIGS. 3C, 3E, 4A, 5A and/or 6. Thus, embodiments described herein provide devices and processes for using a microscope with a tilted objective lens to provide a high-throughput and low cost metrology and tool for non-destructive, non-contact in-line monitoring of both DFR footing defects (e.g., after Figure C) and CTU undercut defects (e.g., after Figure E).

Embodiments described herein provide several advantages compared to the known solutions, such as by providing inspecting for or detecting such defects while being: (1) Non-contact and non-destructive; (2) High resolution; (3) In-line process monitoring capability; (4) Large area inspection; and/or (5) High throughput and significant cost reduction. For instance, embodiments described herein can be used to inspect for DFR footing and CTU for process control and prevention of yield loss and reliability issues during SPTD process development. Embodiments described herein provide a non-destructive non-contact measurement solution for detection of such defects, such as a solution that can be used while or after the traces are formed and prior to subsequent processing of the package. Embodiments described herein can be used without X-ray exposure to substrate 300; without acoustic microscopy exposure to substrate 300; without in-line, physical failure analysis (FA); and/or without cross-section (e.g., physical cutting of the substrate to inspect the interface) which is destructive to the substrate and has low-throughput due to the time required to cut the substrate.

Embodiments described herein may be used to inspect or detect footing and undercut defects in package wafers or diced insulating substrate packages, such as a substrate used in of an electronic device package, a microprocessor package, or a substrate having a surface of dielectric, insulator, or ajinomoto build-up film (ABF). Such substrate may be package substrates upon which a processor or microprocessor will be mounted. Such a packages, wafers or substrates may include through silicon vias (TSV). Such packages may be for packaging logic or memory TSV wafers. In some cases, the packages may be for packaging CPUs, chipsets, graphics chips, or other high density logic device that want to implement 3D stacking (TSV).

Figure 7:
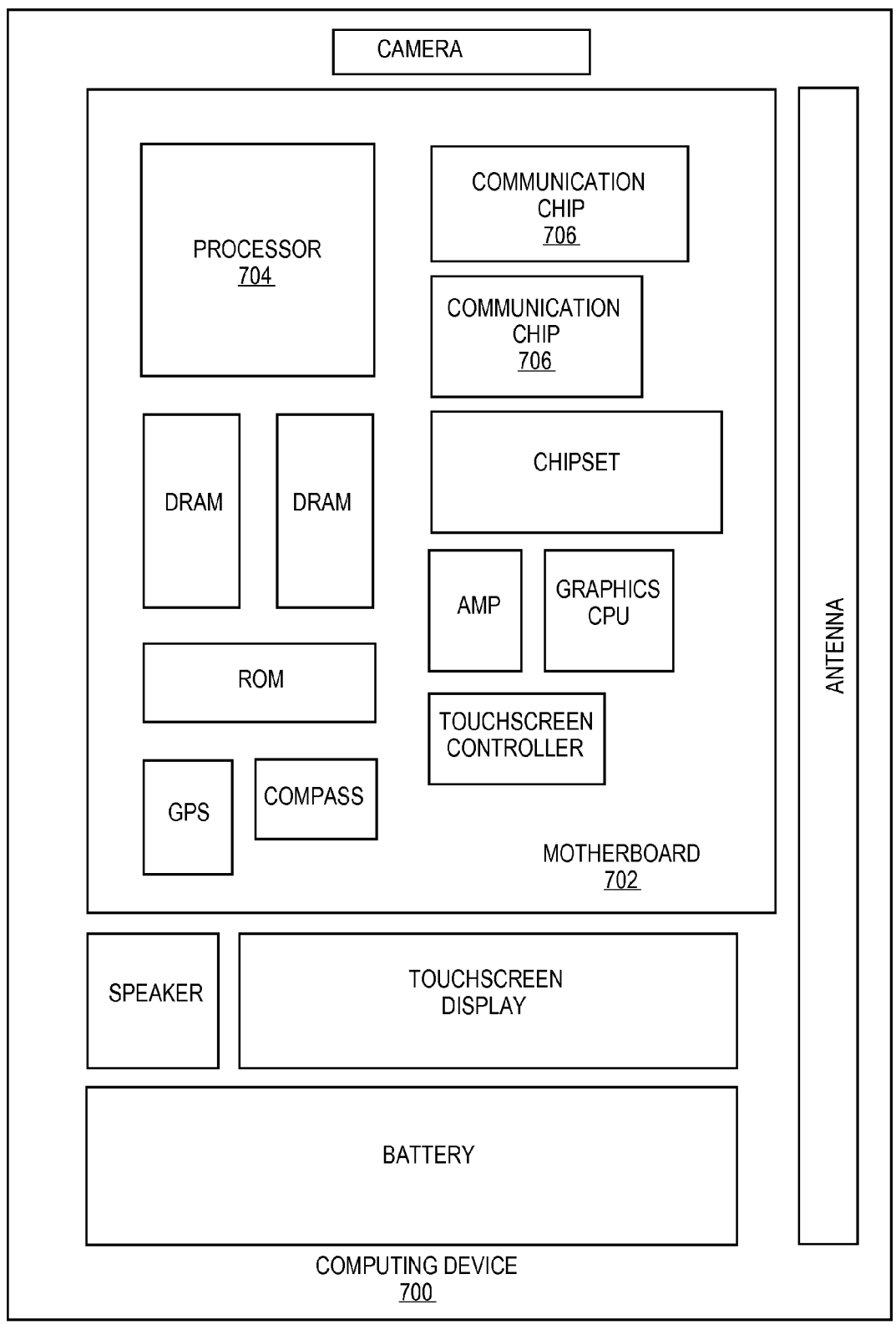
FIG. 7 illustrates a computing device, such as a system on a chip (SoC), in accordance with some implementations.

FIG. 7 illustrates a computing device 700, such as a system on a chip (SoC), in accordance with some implementations. The computing device 700 houses board 702. Board 702 may include a number of components, including but not limited to processor 704 and at least one communication chip 706. Processor 704 is physically and electrically connected to board 702, such as using or through a processor package which may include substrate 300, or a packaging substrate which may have been inspected using embodiments of a microscope having a tilted objective lens described herein for defects 326 and/or defects 344, as noted herein. In some implementations at least one communication chip 706 is also physically and electrically connected to board 702, such as using or through a processor package which may include substrate 300, or a packaging substrate which may have been inspected using embodiments of a microscope having a tilted objective lens described herein for defects 326 and/or defects 344, as noted herein. In further implementations, communication chip 706 is part of processor 704.

In some cases, FIG. 7 illustrates a computing device 700 including a system on a chip (SoC) 702, in accordance with one implementation. In some cases, FIG. 7 shows an example of a system on a chip (SoC) technology (e.g., motherboard 702). Such a SoC may include a microprocessor or CPU, as well as various other components, including electronics and transistors for power and battery regulation; radio frequency (RF) processing, receipt and transmission; voltage regulation; power management; and possibly other systems such as those that may be found in a cellular telephone, etc. FIG. 7 may include one or more additional processors or chips mounted on board 702 or on another component such as a different card or PCB, such as using or through a processor package which may include substrate 300, or a packaging substrate which may have been inspected using embodiments of a microscope having a tilted objective lens described herein for defects 326 and/or defects 344, as noted herein.

Depending on its applications, computing device 700 may include other components that may or may not be physically and electrically connected to board 702. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth).

Communication chip 706 enables wireless communications for the transfer of data to and from computing device 700. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. Communication chip 706 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. Computing device 700 may include a plurality of communication chips 706. For instance, a first communication chip 706 may be dedicated to shorter range wireless communications such as Wi-Fi and Bluetooth and a second communication chip 706 may be dedicated to longer range wireless communications such as GPS, EDGE, GPRS, CDMA, WiMAX, LTE, Ev-DO, and others.

Processor 704 of computing device 700 includes an integrated circuit die packaged within processor 704. In some implementations, the integrated circuit die is packaged within, using or through a processor package which may include substrate 300, or a packaging substrate which may have been inspected using embodiments of a microscope having a tilted objective lens described herein for defects 326 and/or defects 344, as noted herein, thus providing more stable and solidly bonded conductive traces on a packaging substrate, as noted herein, such as with reference to FIGS. 2-6. The term "processor" may refer to any device or portion of a device that processes electronic data from registers and/or memory to transform that electronic data into other electronic data that may be stored in registers and/or memory. In some cases, processor 704 may be a SoC.

Communication chip 706 also includes an integrated circuit die packaged within communication chip 706. In some implementations, this integrated circuit die is packaged within, using or through a processor package which may include substrate 300, or a packaging substrate which may have been inspected using embodiments of a microscope having a tilted objective lens described herein for defects 326 and/or defects 344, as noted herein, thus providing more stable and solidly bonded conductive traces on a packaging substrate, as noted herein, such as with reference to FIGS. 2-6.

In various implementations, computing device 700 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, computing device 700 may be any other electronic device that processes data.

Examples

The following examples pertain to embodiments.

Example 1 is a method for detecting defects in an interface between conductive traces and a insulating substrate surface comprising: forming dry film resist (DFR) islands on an insulating substrate surface; tilting an object lens of a white light interferometer (WLI) microscope to put an axis of the object lens at a first inspection angle of between 2 and 20 degrees with respect to a tangent of the insulating substrate surface; and inspecting the insulating substrate surface and side surfaces of the DFR islands for DFR footing defects using the tilted object lens.

In Example 2, the subject matter of Example 1 can optionally include, wherein inspecting the insulating substrate surface and side surfaces of the DFR islands includes moving the insulating substrate surface with respect to the object lens, in a direction across the side surfaces of the DFR islands.

In Example 3, the subject matter of Example 1 can optionally be further comprising, after inspecting for DFR footing defects: plating conductor between the DFR islands and etching to remove the DFR islands to form conductor traces from the plated conductor; tilting an object lens of a white light interferometer (WLI) microscope to put an axis of the object lens at a second inspection angle of between 5 and 20 degrees with respect to a tangent of the insulating substrate surface; and inspecting the insulating substrate surface and side surfaces of the traces for conductor trace undercut (CTU) defects using the tilted object lens.

In Example 4, the subject matter of Example 3 can optionally include, wherein inspecting the insulating substrate surface and side surfaces of the traces includes moving the insulating substrate surface with respect to the object lens, in a direction across the side surfaces of the traces.

In Example 5, the subject matter of Example 3 can optionally include, wherein tilting the object lens at the first inspection angle comprises one of tilting the entire microscope or tiling only the object lens of the microscope; and wherein tilting the object lens at the second inspection angle comprises (1) one of tilting the entire microscope or tiling only the object lens of the microscope, and (2) tilting the insulating substrate surface.

In Example 6, the subject matter of Example 3 can optionally include, wherein tilting to inspect for DFR footing defects includes tilting to put an axis of the object lens at an angle between 2 and 5 degrees with respect to a tangent of the insulating substrate surface; and wherein tilting to inspect for CTU defects includes tilting to put an axis of the object lens at an angle of between 5 and 10 degrees with respect to a tangent of the insulating substrate surface.

In Example 7, the subject matter of Example 3 can optionally include, wherein inspecting for DFR footing defects occurs during in-line formation of a processor package including the insulating substrate surface, occurs after forming the DFR islands, and occurs prior to plating conductor between the islands; and wherein inspecting for CUT defects occurs during in-line formation of a processor package including the insulating substrate surface, occurs after formation of the conductive traces, and occurs prior to forming material over the conductor traces.

In Example 8, the subject matter of Example 3 can optionally include, wherein inspecting for DFR footing or CUT defects includes creating a three-dimensional X,Y surface profile image having a Z resolution between 1 nm and 2 nm of the insulating substrate surface and DFR island sidewalls or conductor trace sidewalls.

In Example 9, the subject matter of Example 1 can optionally include, wherein inspecting for DFR footing defects or CUT defects includes imaging at a Z-resolution capable of imaging one of a DFR footing defect or a CTU defect having a height of between 200 nm and 2 microns; and a width of between 200 nm and 2 microns.

In Example 10, the subject matter of Example 1 can optionally include, wherein inspecting for DFR footing defects includes rotating one of (1) the insulating substrate surface or (2) the WLI, with respect to the Z axis of the insulating substrate surface, by an angle of one of 90 degrees, 180 degrees or 270 degrees.

In Example 11, the subject matter of Example 1 can optionally include, wherein the insulating substrate surface is part of a substrate package upon which a microprocessor can be mounted or bonded.

In Example 12, the subject matter of Example 1 can optionally include, wherein inspecting inspect for DFR footing defects includes inspecting during in-line formation using a line by line fan beam scan performed by the WLI.

Example 13 is an apparatus for detecting defects in an interface between conductive traces and a insulating substrate surface comprising: a white light interferometer (WLI) microscope having an object lens disposed above a platform surface configured for mounting a package substrate, the object lens capable of being tilted at an angle to put an axis of the object lens at a first inspection angle of between 2 and 20 degrees with respect to a tangent of the platform surface.

In Example 14, the subject matter of Example 13 can optionally be further comprising: a moving tool for moving the platform surface laterally with respect to the microscope; and a camera for imaging the platform surface through the microscope while moving the platform surface.

In Example 15, the subject matter of Example 13 can optionally include, further comprising the platform capable of being tilted at an angle to put an axis of the object lens at a first inspection angle of between 5 and 20 degrees with respect to a tangent of the platform surface.

In Example 16, the subject matter of Example 13 can optionally include, wherein the platform surface is configured for mounting a package substrate having dry film resist islands or conductive traces on an insulating substrate surface.

Example 17 is a system for detecting defects in an interface between conductive traces and a insulating substrate surface comprising: a platform surface for mounting a package substrate having dry film resist islands on an insulating substrate surface; and a white light interferometer (WLI) microscope having an object lens disposed above the platform surface, the object lens capable of being tilted at an angle to put an axis of the object lens at a first inspection angle of between 2 and 20 degrees with respect to a tangent of the platform surface.

In Example 18, the subject matter of Example 17 can optionally be further comprising: a moving tool for moving the platform surface laterally with respect to the microscope; and a camera for imaging through the microscope, one of the platform surface or the insulating substrate surface while moving the platform surface.

In Example 19, the subject matter of Example 17 can optionally include, further comprising the platform capable of being tilted at an angle to put an axis of the object lens at a first inspection angle of between 5 and 20 degrees with respect to a tangent of the platform surface.

In Example 20, the subject matter of Example 19 can optionally include, further comprising, wherein the platform surface is for mounting a package substrate having conductive traces on an insulating substrate surface.

It should also be appreciated that reference throughout this specification to "one embodiment", "an embodiment", "one or more embodiments", or "different embodiments", for example, means that a particular feature may be included in the practice of the embodiments. Similarly, it should be appreciated that in the description various features are sometimes grouped together in a single embodiment, figure, or description thereof for the purpose of streamlining the disclosure and aiding in the understanding of various inventive aspects of embodiments. This method of disclosure, however, is not to be interpreted as reflecting an embodiment that requires more features than are expressly recited in each claim. Rather, as the following claims reflect, inventive aspects of embodiments that may lie in less than all features of a single disclosed embodiment. For example, although the descriptions and figures above describe using tilted objective lens embodiments with respect to an insulating substrate surface, it may be possible to include tilted objective lens embodiments in a system with a platform to hold the substrate, but without the substrate itself (e.g., such as a system to be sold to or used by others). Thus, the claims following the Detailed Description are hereby expressly incorporated into this Detailed Description, with each claim standing on its own as a separate embodiment of the invention.

The invention claimed is:

1. A method for detecting defects in an interface between conductive traces and an insulating substrate surface, the method comprising:
    forming dry film resist (DFR) islands on the insulating substrate surface;
    tilting an object lens of a white light interferometer (WLI) microscope to put an axis of the object lens at a first inspection angle of between 2 and 20 degrees with respect to a tangent of the insulating substrate surface; and
    inspecting the insulating substrate surface and side surfaces of the DFR islands for DFR footing defects using the tilted object lens at the first inspection angle.

2. The method of claim 1, wherein inspecting the insulating substrate surface and side surfaces of the DFR islands includes moving the insulating substrate surface with respect to the object lens, in a direction across the side surfaces of the DFR islands.

3. The method of claim 1, further comprising, after inspecting for DFR footing defects:
    plating conductor between the DFR islands and etching to remove the DFR islands to form conductor traces from the plated conductor;
    tilting an object lens of a white light interferometer (WLI) microscope to put an axis of the object lens at a second inspection angle of between 5 and 20 degrees with respect to a tangent of the insulating substrate surface; and
    inspecting the insulating substrate surface and side surfaces of the traces for conductor trace undercut (CTU) defects using the tilted object lens at the second inspection angle.

4. The method of claim 3, wherein inspecting the insulating substrate surface and side surfaces of the traces includes moving the insulating substrate surface with respect to the object lens, in a direction across the side surfaces of the traces.

5. The method of claim 3, wherein tilting the object lens at the first inspection angle comprises one of tilting the entire microscope or tiling only the object lens of the microscope; and
    wherein tilting the object lens at the second inspection angle comprises (1) one of tilting the entire microscope or tilting only the object lens of the microscope, and (2) tilting the insulating substrate surface.

6. The method of claim 3, wherein tilting to inspect for DFR footing defects includes tilting to put an axis of the object lens at an angle between 2 and 5 degrees with respect to a tangent of the insulating substrate surface; and
    wherein tilting to inspect for CTU defects includes tilting to put an axis of the object lens at an angle of between 5 and 10 degrees with respect to a tangent of the insulating substrate surface.

7. The method of claim 3, wherein inspecting for DFR footing defects occurs during in-line formation of a processor package including the insulating substrate surface, occurs after forming the DFR islands, and occurs prior to plating conductor between the islands; and
    wherein inspecting for CTU defects occurs during in-line formation of a processor package including the insulating substrate surface, occurs after formation of the conductive traces, and occurs prior to forming material over the conductor traces.

8. The method of claim 3, wherein inspecting for DFR footing or CTU defects includes creating a three-dimensional X,Y surface profile image having a Z resolution between 1 and 2 nanometers (nm) of the insulating substrate surface and DFR island sidewalls or conductor trace sidewalls.

9. The method of claim 1, wherein inspecting for DFR footing defects or CTU defects includes imaging at a Z-resolution capable of imaging one of a DFR footing defect or a CTU defect having a height of between 200 nm and 2 microns; and a width of between 200 nm and 2 microns.

10. The method of claim 1, wherein inspecting for DFR footing defects includes rotating one of (1) the insulating substrate surface or (2) the WLI, with respect to the Z axis of the insulating substrate surface, by an angle of one of 90 degrees, 180 degrees or 270 degrees.

11. The method of claim 1, wherein the insulating substrate surface is part of a substrate package upon which a microprocessor can be mounted or bonded.

12. The method of claim 1, wherein inspecting inspect for DFR footing defects includes inspecting during in-line formation using a line by line fan beam scan performed by the WLI.

* * * * *